United States Patent
Clavel

(10) Patent No.: US 11,497,705 B2
(45) Date of Patent: Nov. 15, 2022

(54) ANHYDROUS LIQUID COMPOSITION COMPRISING OILS, A FILM-FORMING POLYMER, A MONOALCOHOL AND A PARTICULATE MATERIAL

(71) Applicant: L'OREAL, Paris (FR)

(72) Inventor: Euriel Clavel, Chevilly Larue (FR)

(73) Assignee: L'OREAL, Paris (FR)

( * ) Notice: Subject to any disclaimer, the term of this patent is extended or adjusted under 35 U.S.C. 154(b) by 766 days.

(21) Appl. No.: 15/762,879

(22) PCT Filed: Sep. 19, 2016

(86) PCT No.: PCT/EP2016/072183
§ 371 (c)(1),
(2) Date: Mar. 23, 2018

(87) PCT Pub. No.: WO2017/050699
PCT Pub. Date: Mar. 30, 2017

(65) Prior Publication Data
US 2018/0263890 A1 Sep. 20, 2018

(30) Foreign Application Priority Data

Sep. 25, 2015 (FR) .................. 1559041

(51) Int. Cl.
| | |
|---|---|
| *A61Q 1/02* | (2006.01) |
| *A61Q 1/04* | (2006.01) |
| *A61Q 1/06* | (2006.01) |
| *A61Q 1/08* | (2006.01) |
| *A61Q 1/10* | (2006.01) |
| *A61K 8/894* | (2006.01) |
| *A61K 8/31* | (2006.01) |
| *A61K 8/34* | (2006.01) |
| *A61K 8/92* | (2006.01) |
| *A61K 8/891* | (2006.01) |

(52) U.S. Cl.
CPC ............... *A61K 8/894* (2013.01); *A61K 8/31* (2013.01); *A61K 8/34* (2013.01); *A61K 8/891* (2013.01); *A61K 8/92* (2013.01); *A61Q 1/02* (2013.01); *A61Q 1/04* (2013.01); *A61Q 1/06* (2013.01); *A61Q 1/08* (2013.01); *A61Q 1/10* (2013.01); *A61K 2800/31* (2013.01)

(58) Field of Classification Search
None
See application file for complete search history.

(56) References Cited

U.S. PATENT DOCUMENTS

| 8,541,009 B2 | 9/2013 | Iida et al. | |
|---|---|---|---|
| 9,233,056 B2 | 1/2016 | Fageon et al. | |
| 2003/0031636 A1 | 2/2003 | Scancarella et al. | |
| 2004/0096407 A1 | 5/2004 | Scancarella et al. | |
| 2006/0057086 A1 | 3/2006 | Scancarella et al. | |
| 2011/0002869 A1* | 1/2011 | Barba ................ | A61Q 1/06 424/70.121 |
| 2011/0129431 A1* | 6/2011 | McDermott ......... | A61Q 1/02 424/78.03 |
| 2014/0296352 A1 | 10/2014 | Arnaud | |
| 2015/0209244 A1* | 7/2015 | Cohen ............. | A61K 8/0241 424/70.7 |
| 2016/0213595 A1* | 7/2016 | Bouarfa ............ | A61K 8/375 |

FOREIGN PATENT DOCUMENTS

| FR | 2 974 367 A1 | 10/2012 |
|---|---|---|
| FR | 3 015 259 A1 | 6/2015 |
| JP | 61-158913 A | 7/1986 |
| JP | 4-1117 A | 1/1992 |
| JP | 4-312511 A | 11/1992 |
| JP | 2000-247630 A | 9/2000 |
| JP | 2011-16734 A | 1/2011 |
| JP | 2014-519482 A | 8/2014 |
| WO | WO 02/094182 A2 | 11/2002 |
| WO | WO 2009/150846 A1 | 12/2009 |
| WO | WO 2013/068236 A1 | 5/2013 |

OTHER PUBLICATIONS

International Search Report dated Oct. 31, 2016 in PCT/EP2016/072183 filed Sep. 19, 2016.

* cited by examiner

*Primary Examiner* — Jyothsna A Venkat
(74) *Attorney, Agent, or Firm* — Oblon, McClelland, Maier & Neustadt, L.L.P.

(57) ABSTRACT

The invention relates to an anhydrous liquid composition, in particular for caring for and/or making up keratinous substances, in particular the skin, comprising, preferably in a physiologically acceptable medium: a) an oily phase comprising: i) at least one non-volatile oil and ii) at least one volatile hydrocarbon oil and b) at least one monoalcohol comprising from 2 to 8 carbon atoms and c) at least one lipophilic film-forming polymer chosen from: (i) silicone resins of MQ type, (ii) silsesquioxane resins, (iii) vinyl polymers grafted with a carbosiloxane dendrimer, (iv) their mixtures, and d) at least one particulate material, the said composition comprising at least 15% by weight of non-volatile oil(s) with respect to the total weight of the composition. The invention also relates to a method for coating keratinous substances, more particularly for making up and/or caring for keratinous substances, such as the skin, characterized in that it comprises the application to the keratinous substances of a composition as defined above.

5 Claims, No Drawings

ANHYDROUS LIQUID COMPOSITION COMPRISING OILS, A FILM-FORMING POLYMER, A MONOALCOHOL AND A PARTICULATE MATERIAL

The invention relates to an anhydrous liquid composition, in particular for caring for and/or making up keratinous substances, in particular the skin, comprising, preferably in a physiologically acceptable medium:
a) an oily phase comprising:
i) at least one non-volatile oil and
ii) at least one volatile hydrocarbon oil and
b) at least one monoalcohol comprising from 2 to 8 carbon atoms and
c) at least one lipophilic film-forming polymer chosen from:
(i) silicone resins of MQ type,
(ii) silsesquioxane resins,
(iii) vinyl polymers grafted with a carbosiloxane dendrimer,
(iv) their mixtures, and
d) at least one particulate material, the said composition comprising at least 15% by weight of non-volatile oil(s) with respect to the total weight of the composition.

The invention also relates to a method for coating keratinous substances, more particularly for making up and/or caring for keratinous substances, such as the skin, characterized in that it comprises the application to the keratinous substances of a composition as defined above.

Consumers are increasingly looking for cosmetic make-up or care products which spread easily and rapidly on the skin in the form of a deposit which does not have to be thick but on the contrary should blend in as much as possible with the support.

It is known to a person skilled in the art that liquid products for making up and/or caring for the skin comprising a high content of non-volatile oils and in particular with a high refractive index ($n \geq 1.450$) make it possible to obtain good properties of spreading and penetration into the skin and of comfort and a good lustre.

Mention may be made, as examples of liquid make-up products, of liquid foundations, liquid lip glosses or also, in the care field, moisturizing and emollient oily products or anti-sun oils.

This high content of non-volatile oils has a tendency to result in a feeling of greasiness and of tackiness during application and in a poor hold of the deposit on the skin over time.

In liquid formulations having a high oil content and based on particulate material, such as pigments, it is difficult to keep the said materials in suspension over time; the latter will settle out and form a block which is very difficult to redisperse ("cake").

Patent Application EP 2 699 636 discloses liquid make-up compositions rich in monoalcohol and comprising a lipophilic film-forming polymer chosen from vinyl polymers grafted with a carbosiloxane dendrimer in order to obtain a better hold of the mattness. Liquid alcoholic make-up compositions based on red organic pigments are also known from Patent FR 3005857. These documents do not touch on the problems of using volatile oils at high amounts in the presence of pigments. These compositions comprise low contents of non-volatile oil in the composition and are not fully satisfactory with regard to comfort on application.

There thus exists a need to look for novel liquid care and/or make-up compositions based on a particulate material and having a high content of non-volatile oils which make it possible to substantially reduce, indeed even eliminate, the tacky effect on application, to obtain good properties of spreading and of penetration into the skin and of comfort and a good lustre, and to obtain good properties of hold over time and/or which make it possible to obtain a "clean" sedimentation of the particles reflected by a transparent salting out (without suspended particles) and by an easy and homogeneous redispersion of the cake.

During its research studies, the applicant has discovered, unexpectedly, that these objectives could be achieved by using an anhydrous liquid composition comprising, preferably in a physiologically acceptable medium:
a) an oily phase comprising:
i) at least one non-volatile oil and
ii) at least one volatile hydrocarbon oil and
b) at least one monoalcohol comprising from 2 to 8 carbon atoms with respect to the total weight of the composition and
c) at least one lipophilic film-forming polymer chosen from:
(i) silicone resins of MQ type,
(ii) silsesquioxane resins,
(iii) vinyl polymers grafted with a carbosiloxane dendrimer,
(iv) their mixtures, and
d) at least one particulate material, the said composition comprising at least 15% by weight of non-volatile oil(s) with respect to the total weight of the composition.

This discovery forms the basis of the invention.

Thus, a first subject-matter of the invention is an anhydrous liquid composition, in particular for caring for and/or making up keratinous substances, in particular the skin, comprising, preferably in a physiologically acceptable medium:
a) an oily phase comprising:
i) at least one non-volatile oil and
ii) at least one volatile hydrocarbon oil and
b) at least one monoalcohol comprising from 2 to 8 carbon atoms with respect to the total weight of the composition and
c) at least one lipophilic film-forming polymer chosen from:
(i) silicone resins of MQ type,
(ii) silsesquioxane resins,
(iii) vinyl polymers grafted with a carbosiloxane dendrimer,
(iv) their mixtures, and
d) at least one particulate material, the said composition comprising at least 15% by weight of non-volatile oil(s) with respect to the total weight of the composition.

The invention also relates to a method for coating keratinous substances, more particularly for making up and/or caring for keratinous substances, such as the skin, characterized in that it comprises the application to the keratinous substances of a composition as defined above.

Definitions

In the context of the present invention, the term "keratinous substances" is understood to mean the eyelashes, lips and preferably the skin and more particularly the face, cheeks, outline of the eyes or eyelids.

The term "physiologically acceptable" is understood to mean compatible with the skin and/or its superficial body growths, which exhibits a pleasant colour, odour and feel and which does not generate unacceptable discomfort (tingling, tautness, redness) liable to dissuade the consumer from using this composition.

Within the meaning of the invention, the expression "anhydrous composition" denotes a composition which comprises less than 5% by weight of water, preferably less than 2% by weight of water, indeed even less than 0.5% of water, with respect to its total weight, and in particular a composition which is devoid of water.

The term "particulate material" is understood to mean any compound in the form of particles which are insoluble and dispersible in the composition of the invention, the said material being different from the lipophilic film-forming polymer.

The composition according to the invention is provided in the form of a liquid. The term "liquid composition" is understood to mean a composition which is liquid at ambient temperature (25° C.) and at atmospheric pressure (1.013× $10^5$ Pa) and, more particularly, which exhibits a viscosity ranging from 0.02 to 0.8 Pa·s, preferably ranging from 0.04 to 0.4 Pa·s and more preferably still ranging from 0.04 to 0.1 Pa·s.

The viscosity measurement is generally carried out at 25° C. using a Rheomat RM180 viscometer equipped with a No. 2 spindle, the measurement being carried out after rotating the spindle within the composition for 10 minutes (after which time stabilization of the viscosity and of the rotational speed of the spindle is observed), at 200 revolutions/min (rpm).

Oily Phase

The compositions according to the invention comprise an oily phase.

The oily phase comprises at least one non-volatile oil in a proportion of at least 15.0% by weight, preferably of at least 30.0% by weight and more preferably of at least 45.0% by weight, with respect to the total weight of the composition, and at least one volatile hydrocarbon oil.

The term "oil" is understood to mean any fatty substance in the liquid form at ambient temperature (20-25° C.) and at atmospheric pressure. These oils can be of animal, vegetable, mineral or synthetic origin.

Non-Volatile Oils

The term "non-volatile oil" is understood to mean an oil which remains on the skin or the keratinous fibre at ambient temperature (20-25° C.) and atmospheric pressure for at least several hours, and which in particular has a vapour pressure of less than $10^{-3}$ mmHg (0.13 Pa).

The oil can be chosen from all oils, preferably physiologically acceptable oils, in particular mineral, animal, vegetable or synthetic oils; especially non-volatile hydrocarbon oils and/or non-volatile silicone oils and/or non-volatile fluorinated oils, and their mixtures.

The term "hydrocarbon oil" is understood to mean an oil predominantly comprising carbon and hydrogen atoms, and optionally ester, ether, fluoro, carboxylic acid and/or alcohol groups.

Mention may be made, as examples of non-volatile hydrocarbon oils which can be used in the invention, of:
hydrocarbon oils of vegetable origin, such as triglycerides of fatty acids having from 4 to 24 carbon atoms, such as triglycerides of caprylic/capric acids, such as those sold by Stearinerie Dubois or those sold under the names Miglyol 810®, 812® and 818® by Dynamit Nobel; triglycerides of branched $C_{18}$-$C_{36}$ fatty acids and of glycerol, such as that sold under the name DUB TGI 24® by Stearinerie Dubois (INCI name C18-36 Acid Triglyceride);

linear or branched hydrocarbons of mineral or synthetic origin, such as liquid paraffins and their derivatives, petrolatum, polydecenes, polybutenes, hydrogenated polyisobutene, such as Parleam, or squalane;

synthetic ethers having from 10 to 40 carbon atoms, such as dicaprylyl ether;

synthetic esters, in particular of fatty acids isononyl isononanoate, isopropyl myristate, isopropyl palmitate, $C_{12}$ to $C_{15}$ alkyl benzoate, hexyl laurate, diisopropyl adipate, 2-ethylhexyl palmitate, 2-octyldodecyl stearate, 2-octyldodecyl erucate, isostearyl isostearate, diisostearyl malate or tridecyl trimellitate;

fatty alcohols which are liquid at ambient temperature, comprising a branched and/or unsaturated carbon chain having from 12 to 26 carbon atoms, such as octyldodecanol, isostearyl alcohol, 2-butyloctanol, 2-hexyldecanol, 2-undecylpentadecanol or oleyl alcohol;

higher fatty acids, such as oleic acid, linoleic acid or linolenic acid;

carbonates, such as dicaprylyl carbonate;

acetates;

citrates;

fluorinated oils which are optionally partially hydrocarbon-based and/or silicone-based, for instance fluorosilicone oils, fluorinated polyethers or fluorinated silicones, such as described in the document EP-A-847 752;

silicone oils, such as non-volatile polydimethylsiloxanes (PDMSs); phenylated silicones, such as phenyl trimethicones, phenyl dimethicones, phenyl(trimethylsiloxy) diphenylsiloxanes, diphenyl dimethicones, diphenyl (methyldiphenyl)trisiloxanes or (2-phenylethyl) trimethylsiloxysilicates, and their mixtures.

Preferably, the oily phase of the composition according to the invention comprises at least one non-volatile oil having a refractive index n of greater than or equal to 1.450. The refractive index is measured at ambient temperature (20° C.) and atmospheric pressure. The said non-volatile oil is chosen in particular from:

non-volatile hydrocarbon oils having a refractive index of greater than or equal to 1.450, non-volatile phenylated silicones having a refractive index of greater than or equal to 1.450, and their mixtures.

Mention may in particular be made, as hydrocarbon oils with a refractive index n of greater than or equal to 1.450, of:

linear or branched hydrocarbons of mineral or synthetic origin, in particular polybutenes, such as the commercial products Indopol H 100 (n=1.49) and Indopol H 1500® (n=1.5) from INEOS, or hydrogenated polyisobutenes, such as the commercial products Parleam HV® (n=1.456) and Parleam SV® (n=1.458) from NOF Corporation;

synthetic esters of fatty acids, such as isostearyl lactate, isostearyl palmitate, octyldodecyl neodecanoate, isocetyl stearate, propylene glycol monoisostearate, 2-ethylhexyl isostearate, octyldodecyl stearate, octyldodecyl myristate, diisostearyl adipate, octyl hydroxystearate, glyceryl triisostearate, octyldodecyl stearoylstearate, diisocetyl dodecanedioate, dipentaerythrityl hexacaprylate/hexacaprate, 2-octyldodecyl hydroxystearate, pentaerythrityl tetra(octyldodecanoate), triisostearyl citrate, pentaerythrityl tetra(2-hexyldecanoate), propylene glycol diisostearate, tridecyl tetradecanoin, isostearyl isostearate, isofol 24 isostearate, triisocetyl citrate, diisopropyl dimer dilinoleate, pentaerythrityl tetra (decyltetradecanoate), diisostearyl malate, diisoarachidyl dodecanedioate, octyldodecyl erucate, triisoarachidyl citrate, hexyldecyl myristoyl methylaminopropionate, pentaerythrityl tetraisostearate, trimethylolpropane triisostearate, oleyl erucate, ditrimethylolpropane tetraisostearate, dioctyldodecyl dimer dilinoleate, ethyl panthenol, sucrose 6-8 soya fatty chains, triisostearyl trilinoleate, 2-octyldodecyl benzoate, 2-ethylhexyl benzoate, isofol 12 trimellitate, $C_{12}$-$C_{15}$ alkyl benzoate, hydrogenated dimer dilinoleyl/dimethylcarbonate copolymer, triisodecyl trimellitate, tridecyl trimellitate, tri(2-ethylhexyl) trimellitate, castor oil benzoate, dipropylene glycol dibenzoate or 2-ethylhexyl glyceryl ether palmitate;

hydrocarbon oils of vegetable origin, such as triglycerides of branched $C_{18}$-$C_{36}$ fatty acids and of glycerol (n=1.454-1.458), arara oil, jojoba oil, pracaxi oil, virgin olive oil, Limnanthes (meadowfoam) oil, sesame seed oil, Ximenia oil, soybean oil, macadamia oil or castor oil;

oils comprising polyoxypropylene (POP) or polyoxyethylene (POE) groups, such as oxypropylenated (3 OP) dimyristyl adipate, oxyethylenated (7 OE) glyceryl triacetate, PEG-4 (4 OE), PEG-6 (6 OE), PEG-8 (8 OE) or octyldodecyl/PPG-3 myristyl ether dimer dilinoleate;

their mixtures.

The hydrocarbon oil or oils with a refractive index n of greater than or equal to 1.450 will more particularly be chosen from:

triglycerides of branched $C_{18}$-$C_{36}$ fatty acids (n=1.46) and of glycerol, such as the commercial product DUB TGI 24® from Stearineries Dubois, diisostearyl malate (n=1.46), such as the commercial product Schercemol DISM Ester® from Lubrizol, tridecyl trimellitate (n=1.48), such as the commercial product Liponate TDTM® from Vantage Specialty Chemicals, and their mixtures.

According to a specific form of the invention, use is made, as hydrocarbon oils with a refractive index n of greater than or equal to 1.450, of a mixture of triglycerides of branched $C_{18}$-$C_{36}$ fatty acids and of glycerol, diisostearyl malate and tridecyl trimellitate.

Mention may in particular be made, as non-volatile silicone oils with a refractive index of greater than or equal to 1.450, of phenylated silicones.

The term "phenylated silicone" (also referred to as phenylated silicone oil) is understood to mean an organopolysiloxane substituted with at least one phenyl group.

The phenylated silicone oil can be chosen from phenyl trimethicones, phenyl dimethicones, phenyl(trimethylsiloxy)diphenylsiloxanes, diphenyl dimethicones, diphenyl (methyldiphenyl)trisiloxanes, trimethylpentaphenyltrisiloxane or (2-phenylethyl)tri methylsiloxysilicates.

The silicone oil can correspond to the formula:

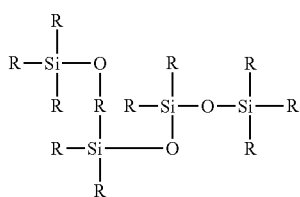

in which the R groups represent, independently of one another, a methyl or a phenyl. Preferably, in this formula, the silicone oil comprises at least three phenyl groups, for example at least four, at least five or at least six.

According to another embodiment, the silicone oil corresponds to the formula:

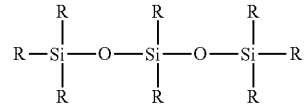

in which the R groups represent, independently of one another, a methyl or a phenyl. Preferably, in this formula, the said organopolysiloxane comprises at least three phenyl groups, for example at least four or at least five.

Mixtures of the phenylated organopolysiloxanes described above can be used.

Mention may be made, for example, of mixtures of triphenylated, tetraphenylated or pentaphenylated organopolysiloxane.

According to another embodiment, the silicone oil corresponds to the formula:

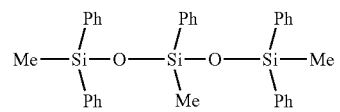

in which Me represents methyl and Ph represents phenyl. Such a phenylated silicone is in particular manufactured by Dow Corning under the reference Dow Corning 555 Cosmetic Fluid (INCI name: trimethyl pentaphenyl trisiloxane). The reference Dow Corning 554 Cosmetic Fluid can also be used.

According to another embodiment, the silicone oil corresponds to the formula:

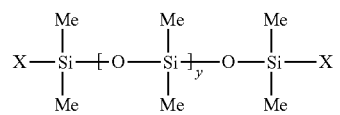

in which Me represents methyl, y is between 1 and 1000 and X represents —$CH_2$—$CH(CH_3)$(Ph).

According to another embodiment, the silicone oil corresponds to the formula:

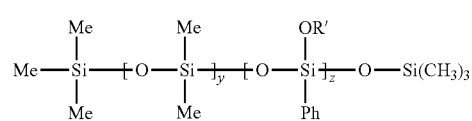

in which —OR' represents —O—$SiMe_3$, y is between 1 and 1000 and z is between 1 and 1000.

The phenylated silicone oil can be chosen from the phenylated silicones of following formula (VI):

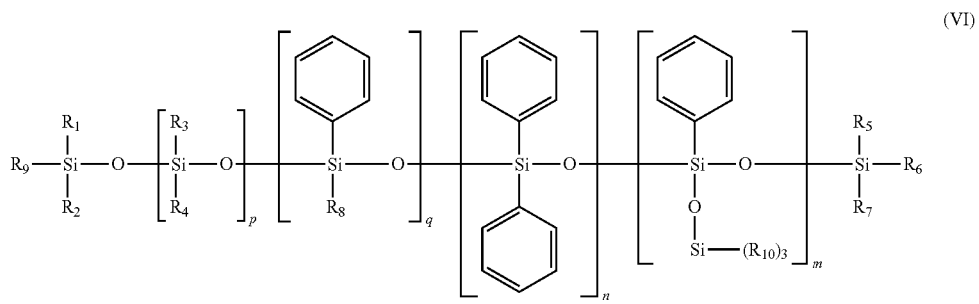

in which:
R$_1$ to R$_{10}$, independently of one another, are saturated or unsaturated, linear, cyclic or branched, C$_1$-C$_{30}$ hydrocarbon radicals,
m, n, p and q are, independently of one another, integers between 0 and 900, with the proviso that the sum "m+n+q" is other than 0.

Preferably, the sum "m+n+p+q" is between 1 and 100. Preferably, the sum "m+n+p+q" is between 1 and 900 and better still between 1 and 800. Preferably, q is equal to 0.

The phenylated silicone oil can be chosen from the phenylated silicones of following formula (VII):

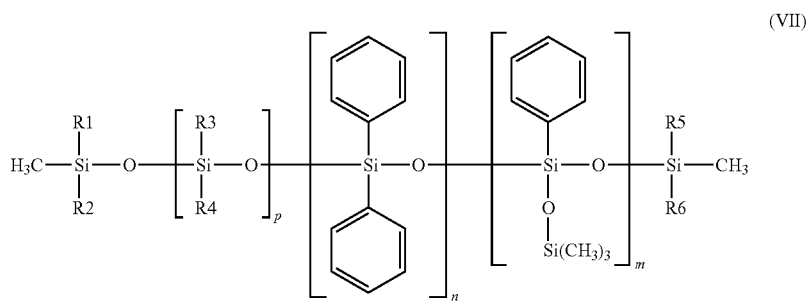

in which:
R$_1$ to R$_6$, independently of one another, are saturated or unsaturated, linear, cyclic or branched, C$_1$-C$_{30}$ hydrocarbon radicals,
m, n and p are, independently of one another, integers between 0 and 100, with the proviso that the sum "n+m" is between 1 and 100.

Preferably, R$_1$ to R$_6$, independently of one another, represent a saturated, linear or branched, C$_1$-C$_{30}$ and in particular C$_1$-C$_{12}$ hydrocarbon radical and especially a methyl, ethyl, propyl or butyl radical.

R$_1$ to R$_6$ can in particular be identical and in addition can be a methyl radical.

Preferably, it is possible to have m=1 or 2 or 3, and/or n=0 and/or p=0 or 1, in the formula (VII).

Use may be made of a phenylated silicone oil of formula (VI) having a viscosity at 25° C. of between 5 and 1500 mm$^2$/s (i.e. 5 to 1500 cSt) and preferably having a viscosity of between 5 and 1000 mm$^2$/s (i.e. 5 to 1000 cSt).

Use may in particular be made, as phenylated silicone oil of formula (VII), of phenyl trimethicones, such as DC556 from Dow Corning (22.5 cSt) or the Silbione 70663V30 oil from Rhône-Poulenc (28 cSt), or diphenyl dimethicones, such as the Belsil oils, in particular Belsil PDM 1000 (1000 cSt), Belsil PDM 200 (200 cSt) and Belsil PDM 20 (20 cSt) from Wacker. The values in brackets represent the viscosities at 25° C.

According to a specific form of the invention, the non-volatile oily phase can comprise a mixture of one or more non-volatile oils with a refractive index of greater than or equal to 1.450 and of one or more non-volatile oils with a refractive index of less than 1.450.

Mention may in particular be made, as examples of a non-volatile oil with a refractive index of less than 1.450, of synthetic ethers having from 10 to 40 carbon atoms, such as dicaprylyl ether (n=1.43).

According to a specific form of the invention, use is made, as non-volatile hydrocarbon oils, of a mixture of triglycerides of branched C$_{18}$-C$_{36}$ fatty acids and of glycerol, diisostearyl malate, tridecyl trimellitate and dicaprylyl ether.

The non-volatile oil or oils in accordance with the invention are preferably present in a concentration ranging from 15% to 85% by weight and more preferably ranging from 30% to 60% by weight and particularly from 45% to 55% by weight, with respect to the total weight of the composition.

The non-volatile oil or oils with a refractive index n of greater than or equal to 1.450 in accordance with the invention are preferably present in a concentration ranging from 15% to 65% by weight and more preferably ranging from 30% to 60% by weight and particularly from 45% to 55% by weight, with respect to the total weight of the composition.

Volatile Hydrocarbon Oils

The term "volatile oil" is understood to mean, within the meaning of the invention, an oil which is capable of evaporating on contact with the skin or the keratinous fibre in less than one hour, at ambient temperature (20-25° C.) and atmospheric pressure. The volatile oils of the invention are volatile cosmetic oils which are liquid at ambient temperature with a non-zero vapour pressure, at ambient temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

Mention may be made, as examples of volatile hydrocarbon oil which can be used in the invention, of volatile hydrocarbon oils chosen from hydrocarbon oils having from 8 to 16 carbon atoms, in particular $C_8$-$C_{16}$ isoalkanes of petroleum origin (also known as isoparaffins), such as isododecane (also known as 2,2,4,4,6-pentamethylheptane), isodecane or isohexadecane, for example the oils sold under the Isopar or Permethyl trade names, branched $C_8$-$C_{16}$ esters, isohexyl neopentanoate and their mixtures. Use may also be made of other volatile hydrocarbon oils, such as petroleum distillates, in particular those sold under the name Shell Solt by Shell; volatile linear alkanes, such as those described in Patent Application DE10 2008 012 457 from Cognis.

Preference is given, among volatile hydrocarbon oils, to $C_8$-$C_{16}$ isoalkanes, in particular isododecane.

The volatile hydrocarbon oil or oils in accordance with the invention are preferably present in concentrations ranging from 10% to 30% by weight and more particularly ranging from 12% to 25% by weight, with respect to the total weight of the composition.

According to a specific form of the invention, the composition can additionally comprise at least one volatile silicone oil.

Mention may be made, as volatile silicone oils, of volatile linear or cyclic silicone oils, in particular those having a viscosity ≤8 centistokes ($8 \cdot 10^{-6}$ m²/s) and having in particular from 2 to 7 silicon atoms, these silicones optionally comprising alkyl or alkoxy groups having from 1 to 10 carbon atoms. Mention may in particular be made, as volatile silicone oils which can be used in the invention, of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane and their mixtures.

Use will more particularly be made of dodecamethylpentasiloxane.

Monoalcohol

The compositions of the invention comprise at least one monoalcohol comprising from 2 to 8 carbon atoms, in particular from 2 to 6 carbon atoms and especially from 2 to 4 carbon atoms.

The compositions of the invention can comprise one or more monoalcohol(s).

This monoalcohol can be represented, for example, by the formula RaOH, in which Ra represents a linear or branched alkyl group comprising from 2 to 8 carbon atoms.

Mention may be made, as monoalcohol, of ethanol, isopropanol, propanol or butanol.

According to one embodiment, the compositions of the invention comprise ethanol.

The amount of monoalcohol(s) is preferably at least 8% by weight and more preferably at least 10% by weight, with respect to the total weight of the said composition.

According to an advantageous embodiment, the amount of monoalcohol(s) ranges from 8% to 40% by weight, preferably from 10% to 20% by weight and more preferably still from 10% to 15% by weight, with respect to the total weight of the said composition.

According to an advantageous embodiment, the monoalcohol/volatile hydrocarbon oil ratio by weight is greater than 1/1, preferably ranging from 1.1/1 to 3/1 and more particularly from 1.2/1 to 1.5/1.

Lipophilic Film-Forming Polymer

The lipophilic film-forming polymer which can be used in the compositions in accordance with the invention are chosen from:
(i) silicone resins of MQ type;
(ii) silsesquioxane resins;
(iii) vinyl polymers grafted with a carbosiloxane dendrimer;
(iv) their mixtures.

The term "polymer" is understood here to mean a compound having one or more repeat unit(s) and preferably at least 2 repeat units.

The term "film-forming polymer" is understood to mean a polymer capable of forming, by itself alone or in the presence of an auxiliary film-forming agent, a macroscopically continuous film which adheres to keratinous substances, preferably a cohesive film, and better still a film, the cohesion and the mechanical properties of which are such that the said film can be isolable and manipulable in isolation, for example when the said film is prepared by pouring onto a non-stick surface, such as a Teflon-coated or silicone-coated surface.

The film-forming polymers of the invention are lipophilic, in particular fat-soluble or fat-dispersible, that is to say soluble or dispersible in oils.

The term "fat-soluble" or "fat-dispersible" is understood to mean the possibility of dissolving the polymer or of dispersing it homogeneously in at least one oil, at ambient temperature or, if appropriate, while heating to a temperature below the flash point of the said oil, and at a percentage by weight generally of less than or equal to 80% by weight of film-forming polymer.

Silicone Resins of MQ Type

More generally, the term "resin" is understood to mean a compound, the structure of which is three-dimensional.

"Silicone resins" are also known as "siloxane resins". Thus, within the meaning of the present invention, a polydimethylsiloxane is not a silicone resin.

The nomenclature of silicone resins (also known as siloxane resins) is known under the name "MDTQ", the resin being described as a function of the various siloxane monomer units it comprises, each of the letters "MDTQ" characterizing a type of unit.

The letter "M" represents the Monofunctional unit of formula $R^1R^2R^3SiO_{1/2}$, the silicon atom being connected to only one oxygen atom in the polymer comprising this unit.

The letter "D" signifies a Difunctional unit $R^1R^2SiO_{2/2}$ in which the silicon atom is connected to two oxygen atoms.

The letter "T" represents a Trifunctional unit of formula $R^1SiO_{3/2}$.

Finally, the letter "Q" signifies a tetrafunctional unit $SiO_{4/2}$ in which the silicon atom is bonded to four oxygen atoms, which are themselves bonded to the remainder of the polymer.

In the M, D and T units defined above, $R^1$, $R^2$ and $R^3$ represent a hydrocarbon radical (in particular an alkyl radical) having from 1 to 10 carbon atoms, a phenyl group, a phenylalkyl group or else a hydroxyl group.

Such resins are described, for example, in the Encyclopedia of Polymer Science and Engineering, vol. 15, John Wiley and Sons, New York, (1989), pp. 265-270, and U.S. Pat. Nos. 2,676,182, 3,627,851, 3,772,247, 5,248,739 or else U.S. Pat. Nos. 5,082,706, 5,319,040, 5,302,685 and 4,935,484.

Mention may be made, as examples of silicone resins of MQ type which can be used according to the invention, of the alkylsiloxysilicates of formula $[(R_1)_3SiO_{1/2}]_x(SiO_{4/2})_y$ (MQ units) in which x and y are integers ranging from 50 to 80, and such that the $R_1$ group represents a radical as defined above and is preferably an alkyl group having from 1 to 8 carbon atoms or a hydroxyl group, preferably a methyl group.

Mention may be made, as examples of solid silicone resins of MQ type of trimethylsiloxysilicate type, of those sold under the reference SR1000 by General Electric, under the reference TMS 803 by Wacker, under the name KF-7312J by Shin-Etsu, DC749 or DC593 by Dow Corning.

Mention may also be made, as silicone resins comprising MQ siloxysilicate units, of phenylalkylsiloxysilicate resins, such as phenylpropyldimethylsiloxysilicate (Silshine 151 sold by General Electric). The preparation of such resins is described in particular in U.S. Pat. No. 5,817,302.

Silsesquioxane Resins

Mention may be made, among the silsesquioxane resins which can be used in the compositions in accordance with the invention, of the alkyl silsesquioxane resins which are silsesquioxane homopolymers and/or copolymers having an average siloxane unit of formula $R_{1n}SiO_{(4-n)2}$, where each $R_1$ independently denotes a hydrogen atom or a $C_1$-$C_{10}$ alkyl group, where more than 80 mol % of the $R_1$ radicals represent a $C_3$-$C_{10}$ alkyl group, and n is a number from 1.0 to 1.4, and more particularly use will be made of a silsesquioxane copolymer in which more than 60 mol % comprises $R_1SiO_{3/2}$ units in which $R_1$ has the definition indicated above.

Preferably, the silsesquioxane resin is chosen so that $R_1$ is a $C_1$-$C_{10}$ alkyl group, preferably a $C_1$-$C_4$ alkyl group and more particularly a propyl group. Use will more particularly be made of a poly(propyl silsesquioxane) or t-propyl silsesquioxane resin (INCI name: Polypropylsilsesquioxane (and) Isododecane), such as the product sold under the trade name Dow Corning® 670 Fluid by Dow Corning.

Vinyl Polymers Grafted with a Carbosiloxane Dendrimer

A vinyl polymer suitable for the preparation of a composition according to the invention comprises at least one unit derived from carbosiloxane dendrimer.

The vinyl polymer has a backbone and at least one side chain, which side chain comprises a unit derived from carbosiloxane dendrimer exhibiting a carbosiloxane dendrimer structure.

In the context of the present invention, the term "carbosiloxane dendrimer structure" represents a molecular structure possessing branched groups having high molecular weights, the said structure having high regularity in the radial direction starting from the bond to the backbone. Such carbosiloxane dendrimer structures are described in the form of a highly branched siloxane-silylalkylene copolymer in laid-open Japanese Patent Application Kokai 9-171 154.

A vinyl polymer according to the invention can comprise units derived from carbosiloxane dendrimers which can be represented by the following general formula (I):

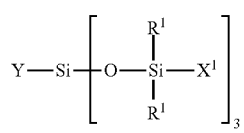

(I)

in which:
$R^1$ represents an aryl group having from 5 to 10 carbon atoms or an alkyl group having from 1 to 10 carbon atoms;
$X^i$ represents a silylalkyl group which, when i=1, is represented by the formula (II):

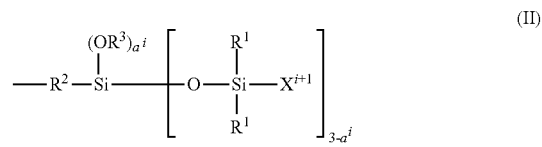

(II)

in which:
$R^1$ is as defined above in the formula (I),
$R^2$ represents an alkylene radical having from 2 to 10 carbon atoms,
$R^3$ represents an alkyl group having from 1 to 10 carbon atoms,
$X^{i+1}$ is chosen from: a hydrogen atom, an alkyl group having from 1 to 10 carbon atoms, an aryl group having from 5 to 10 carbon atoms and a silylalkyl group defined above of formula (II) with i=i+1,
i is an integer from 1 to 10 which represents the generation of the said silylalkyl group, and
$a^i$ is an integer from 0 to 3;
Y represents a radically polymerizable organic group chosen from:
organic groups comprising a methacrylic group or an acrylic group, the said organic groups being represented by the formulae:
in which:

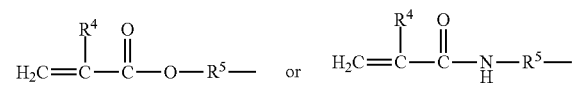

$R^4$ represents a hydrogen atom or an alkyl group having from 1 to 10 carbon atoms; and
$R^5$ represents an alkylene group having from 1 to 10 carbon atoms, such as a methylene group, an ethylene group, a propylene group or a butylene group, methylene and propylene groups being preferred; and
organic groups comprising a styryl group of formula:

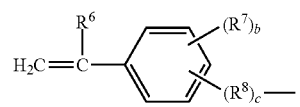

in which:
$R^6$ represents a hydrogen atom or an alkyl group having from 1 to 10 carbon atoms, such as a methyl group, an ethyl group, a propyl group or a butyl group, the methyl group being preferred;
$R^7$ represents an alkyl group having from 1 to 10 carbon atoms;
$R^8$ represents an alkylene group having from 1 to 10 carbon atoms, such as a methylene group, an ethylene group, a propylene group or a butylene group, the ethylene group being preferred;

b is an integer from 0 to 4; and c has the value 0 or 1, so that, if c has the value 0, —$(R^8)_c$— represents a bond.

According to one embodiment, $R^1$ can represent an aryl group possessing from 5 to 10 carbon atoms or an alkyl group possessing from 1 to 10 carbon atoms. The alkyl group can preferably be represented by a methyl group, an ethyl group, a propyl group, a butyl group, a pentyl group, an isopropyl group, an isobutyl group, a cyclopentyl group or a cyclohexyl group. The aryl group can preferably be represented by a phenyl group and a naphthyl group. The methyl and phenyl groups are more particularly preferred, and the methyl group is preferred above all.

According to one embodiment, $R^2$ represents an alkylene group possessing from 2 to 10 carbon atoms, in particular a linear alkylene group, such as an ethylene, propylene, butylene or hexylene group; or a branched alkylene group, such as a methylmethylene, methylethylene, 1-methylpentylene or 1,4-dimethylbutylene group.

Ethylene, methylethylene, hexylene, 1-methylpentylene and 1,4-dimethylbutylene groups are preferred above all.

According to one embodiment, $R^3$ is chosen from methyl, ethyl, propyl, butyl and isopropyl groups.

In the formula (II), i indicates the number of generations and thus corresponds to the number of repetitions of the silylalkyl group.

For example, when the number of generations is equal to 1, the carbosiloxane dendrimer can be represented by the general formula shown below, in which Y, $R^1$, $R^2$ and $R^3$ are as defined above, $R^{12}$ represents a hydrogen atom or is identical to $R^1$ and $a^1$ is identical to $a^i$. Preferably, the total average number of $OR^3$ groups in a molecule is within the range from 0 to 7.

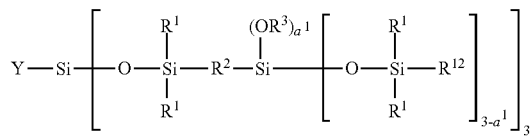

When the number of generations is equal to 2, the carbosiloxane dendrimer can be represented by the general formula below, in which Y, $R^1$, $R^2$, $R^3$ and $R^{12}$ are the same as defined above, and $a^1$ and $a^2$ represent the $a^i$ of the indicated generation. Preferably, the total average number of $OR^3$ groups in a molecule is within the range from 0 to 25.

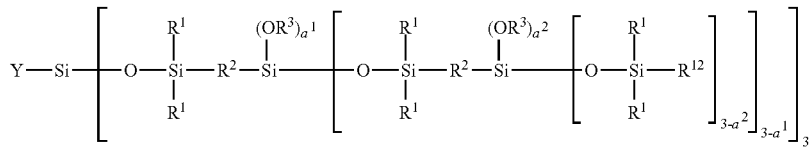

In the case where the number of generations is equal to 3, the carbosiloxane dendrimer is represented by the general formula below, in which Y, $R^1$, $R^2$, $R^3$ and $R^{12}$ are the same as defined above, and $a^1$, $a^2$ and $a^3$ represent the $a^i$ of the indicated generation. Preferably, the total average number of $OR^3$ groups in a molecule is within the range from 0 to 79.

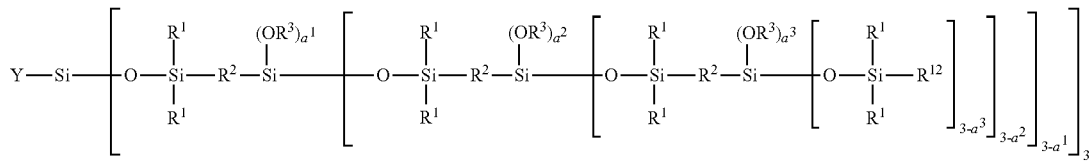

A vinyl polymer having at least one unit derived from carbosiloxane dendrimer possesses a molecular side chain comprising a carbosiloxane dendrimer structure and can result from the polymerization:

(A) of 0 to 99.9 parts by weight of a vinyl monomer, and
(B) of 100 to 0.1 parts by weight of a carbosiloxane dendrimer comprising a radically polymerizable organic group, represented by the general formula (I) as defined above.

The monomer of vinyl type which is the component (A) in the vinyl polymer having at least one unit derived from carbosiloxane dendrimer is a monomer of vinyl type which comprises a radically polymerizable vinyl group.

There is no particular limitation as regards such a monomer.

The following are examples of this monomer of vinyl type: methyl methacrylate, ethyl methacrylate, n-propyl methacrylate, isopropyl methacrylate or a methacrylate of an analogous lower alkyl; glycidyl methacrylate; butyl methacrylate, butyl acrylate, n-butyl methacrylate, isobutyl methacrylate, tert-butyl acrylate, tert-butyl methacrylate, n-hexyl methacrylate, cyclohexyl methacrylate, 2-ethylhexyl acrylate, 2-ethylhexyl methacrylate, octyl methacrylate, lauryl methacrylate, stearyl acrylate, stearyl methacrylate or an analogous higher methacrylate; vinyl acetate, vinyl propionate or a vinyl ester of an analogous lower fatty acid; vinyl caproate, vinyl 2-ethylhexanoate, vinyl laurate, vinyl stearate or an ester of an analogous higher fatty acid; styrene, vinyltoluene, benzyl methacrylate, phenoxyethyl methacrylate, vinylpyrrolidone or analogous vinylaromatic monomers; methacrylamide, N-methylolmethacrylamide, N-methoxymethylmethacrylamide, isobutoxymethoxymethacrylamide, N,N-dimethylmethacrylamide or analogous monomers of vinyl type comprising amide groups; hydroxyethyl methacrylate, hydroxypropyl alcohol methacrylate or analogous monomers of vinyl type which comprise hydroxyl groups; acrylic acid, methacrylic acid, itaconic acid, crotonic acid, fumaric acid, maleic acid or analogous monomers of vinyl type which comprise a carboxylic acid group; tetrahydrofurfuryl methacrylate, butoxyethyl methacrylate, ethoxydiethylene glycol methacrylate, polyethylene glycol methacrylate, polypropylene glycol monomethacrylate, hydroxybutyl vinyl ether, cetyl vinyl ether, 2-ethylhexyl vinyl ether or an analogous monomer of vinyl type with ether bonds; methacryloyloxypropyltrimethoxysilane, polydimethylsiloxane having a methacrylic group on one of its molecular ends, polydimethylsiloxane having a styryl group on one of its molecular ends, or an analogous silicone compound possessing unsaturated groups; butadiene; vinyl chloride; vinylidene chloride; methacrylonitrile; dibutyl fumarate; maleic anhydride; succinic anhydride; methacryl glycidyl ether; an organic salt of an amine, an ammonium salt, and an alkali metal salt of methacrylic acid, of itaconic acid, of crotonic acid, of maleic acid or of fumaric acid; a radically polymerizable unsaturated monomer possessing a sulfonic acid group, such as a styrenesulfonic acid group; a quaternary ammonium salt derived from methacrylic acid, such as 2-hydroxy-3-methacryloyloxypropyltrimethylammonium chloride; and a methacrylic acid ester of an alcohol possessing a tertiary amine group, such as a methacrylic acid ester of diethylamine.

Multifunctional monomers of vinyl type can also be used.

The following represent examples of such compounds: trimethylolpropane trimethacrylate, pentaerythrityl trimethacrylate, ethylene glycol dimethacrylate, tetraethylene glycol dimethacrylate, polyethylene glycol dimethacrylate, 1,4-butanediol dimethacrylate, 1,6-hexanediol dimethacrylate, neopentyl glycol dimethacrylate, trimethylolpropane ethoxylate trimethacrylate, tris(2-hydroxyethyl)isocyanurate dimethacrylate, tris(2-hydroxyethyl)isocyanurate trimethacrylate, polydimethylsiloxane capped with styryl groups possessing divinylbenzene groups on both ends, or analogous silicone compounds possessing unsaturated groups.

A carbosiloxane dendrimer, which is the component (B), can be represented by the formula (I) as defined above.

The following represent the preferred examples of Y group of the formula (I): an acryloyloxymethyl group, a 3-acryloyloxypropyl group, a methacryloyloxymethyl group, a 3-methacryloyloxypropyl group, a 4-vinylphenyl group, a 3-vinylphenyl group, a 4-(2-propenyl)phenyl group, a 3-(2-propenyl)phenyl group, a 2-(4-vinylphenyl) ethyl group, a 2-(3-vinylphenyl)ethyl group, a vinyl group, an allyl group, a methallyl group and a 5-hexenyl group.

A carbosiloxane dendrimer according to the present invention can be represented by the formulae having the following average structures:

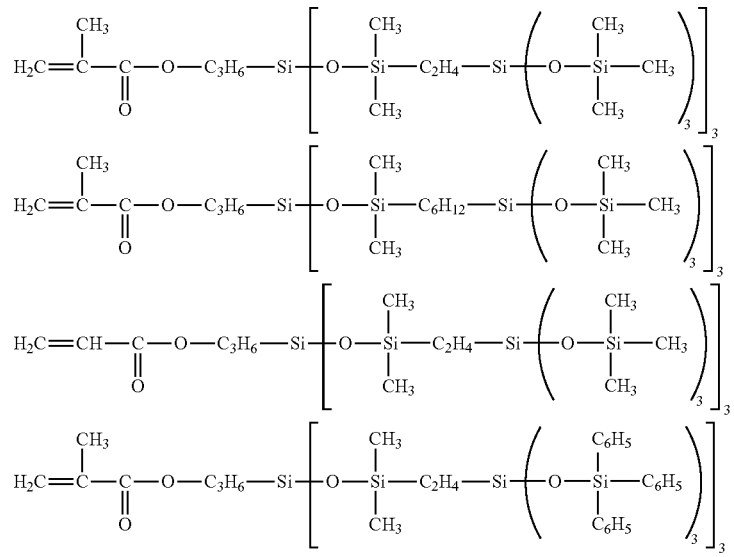

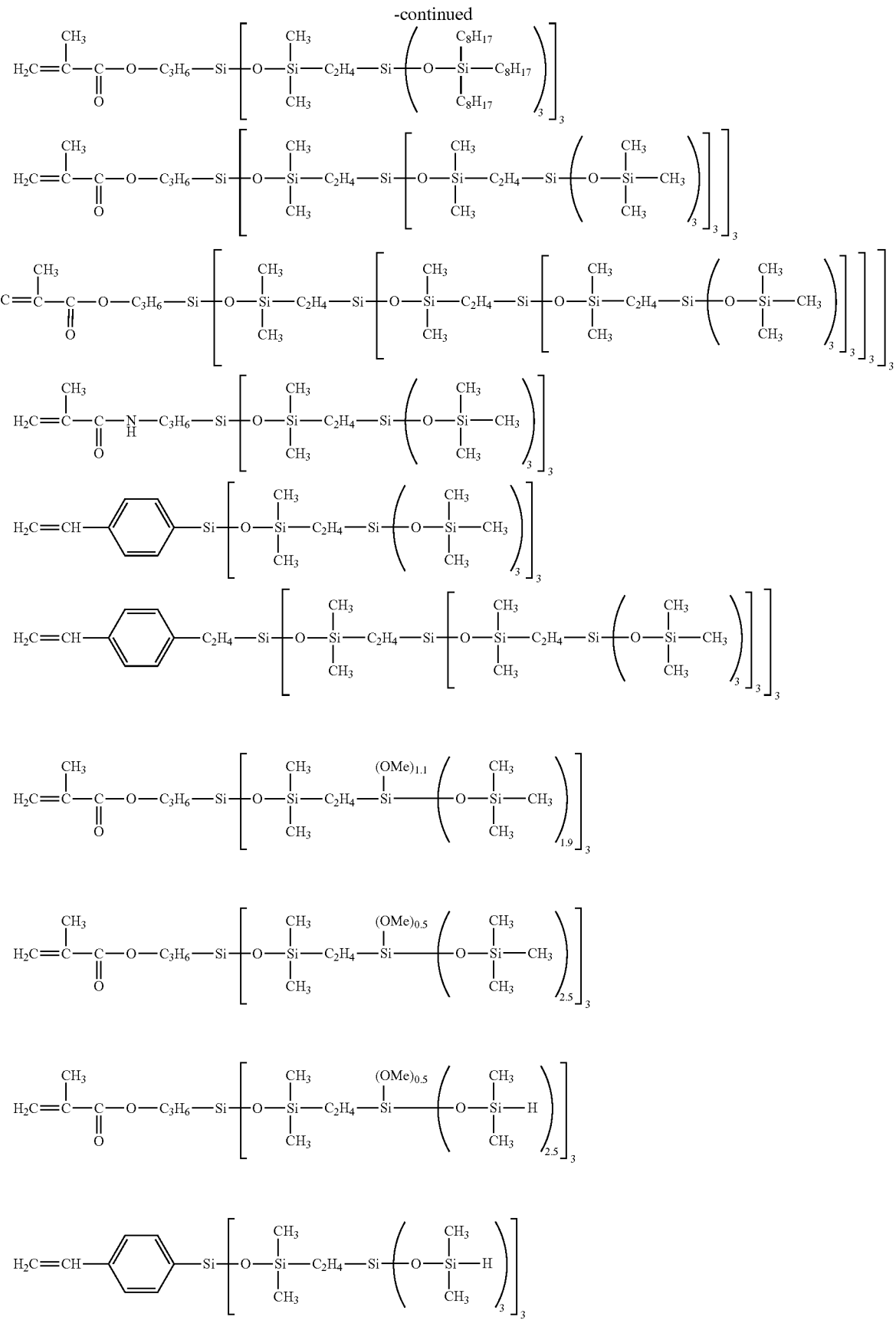

Thus, according to one embodiment, the carbosiloxane dendrimer of the composition according to the present invention is represented by the following formula:

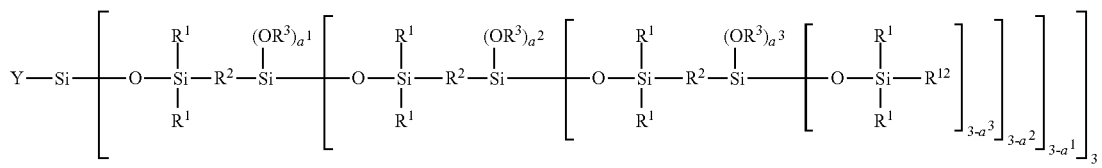

in which:
Y, $R^1$, $R^2$ and $R^3$ are as defined in the formulae (I) and (II) above;
$a^1$, $a^2$ and $a^3$ correspond to the definition of $a^i$ according to the formula (II); and
$R^{12}$ is H, an aryl group having from 5 to 10 carbon atoms or an alkyl group having from 1 to 10 carbon atoms.

According to one embodiment, the carbosiloxane dendrimer of the composition according to the present invention is represented by one of the following formulae:

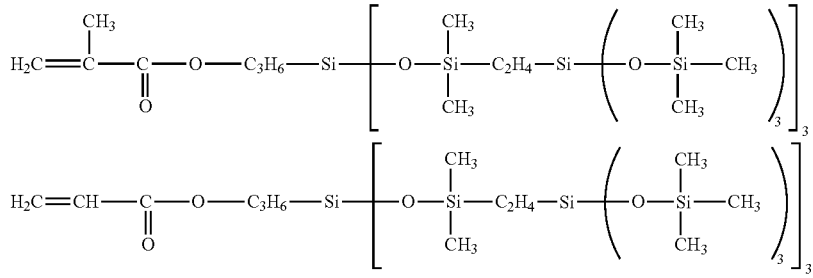

The vinyl polymer comprising the carbosiloxane dendrimer according to the invention can be manufactured according to the process for manufacturing a branched silalkylene siloxane described in Japanese Patent Application Hei 9-171 154.

For example, it can be produced by subjecting, to a hydrosilylation reaction, an organosilicon compound which comprises a hydrogen atom linked to a silicon atom, represented by the following general formula (IV):

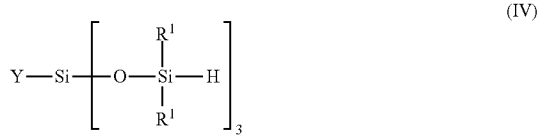

$R^1$ being as defined above in the formula (I),
and an organosilicon compound which comprises an alkenyl group.

In the above formula, the organosilicon compound can be represented by (3-methacryloyloxypropyl)tris(dimethylsiloxy)silane, (3-acryloyloxypropyl)tris(dimethylsiloxy)silane and (4-vinylphenyl)tris(dimethylsiloxy)silane. The organosilicon compound which comprises an alkenyl group can be represented by vinyltris(trimethylsiloxy)silane, vinyltris(dimethylphenylsiloxy)silane and (5-hexenyl)tris(trimethylsiloxy)silane.

The hydrosilylation reaction is carried out in the presence of a chloroplatinic acid, of a complex of vinylsiloxane and of platinum, or of an analogous transition metal catalyst.

A vinyl polymer having at least one unit derived from carbosiloxane dendrimer can be chosen from polymers such that the unit of a derivative of a carbosiloxane dendrimer is a carbosiloxane dendritic structure represented by the formula (III):

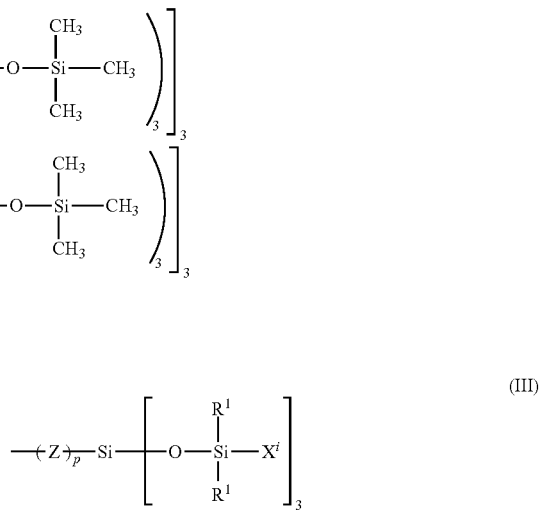

in which Z is a divalent organic group, "p" is 0 or 1, $R^1$ is as defined above in the formula (IV) and Xi is a silylalkyl group represented by the formula (II) as defined above.

In a vinyl polymer having at least one unit derived from carbosiloxane dendrimer, the polymerization ratio of the component (A) to the component (B), in terms of the ratio by weight of (A) to (B), is within a range from 0/100 to 99.9/0.1, indeed even from 0.1/99.9 to 99.9/0.1 and preferably within a range from 1/99 to 99/1. A ratio of the component (A) to the component (B) of 0/100 means that the compound becomes a homopolymer of component (B).

A vinyl polymer having at least one unit derived from carbosiloxane dendrimer can be obtained by the copolymerization of the components (A) and (B) or by the polymerization of the component (B) alone.

The polymerization can be a radical polymerization or an ionic polymerization; however, the radical polymerization is preferred.

The polymerization can be carried out by bringing about a reaction between the components (A) and (B) in a solution for a period of 3 to 20 hours in the presence of a radical initiator at a temperature of 50° C. to 150° C.

A suitable solvent for this purpose is hexane, octane, decane, cyclohexane or an analogous aliphatic hydrocarbon; benzene, toluene, xylene or an analogous aromatic hydrocarbon; diethyl ether, dibutyl ether, tetrahydrofuran, dioxane or ethers; acetone, methyl ethyl ketone, methyl isobutyl ketone, diisobutyl ketone or analogous ketones; methyl acetate, ethyl acetate, butyl acetate, isobutyl acetate or analogous esters; methanol, ethanol, isopropanol, butanol or analogous alcohols; octamethylcyclotetrasiloxane, decamethylcyclopentasiloxane, hexamethyldisiloxane, octamethyltrisiloxane or an analogous organosiloxane oligomer.

A radical initiator can be any compound known in the art for conventional radical polymerization reactions. The specific examples of such radical initiators are 2,2'-azobis (isobutyronitrile), 2,2'-azobis(2-methylbutyronitrile), 2,2'-azobis(2,4-dimethylvaleronitrile) or analogous compounds of azobis type; benzoyl peroxide, lauroyl peroxide, tert-butyl peroxybenzoate, tert-butyl peroxy-2-ethylhexanoate or an analogous organic peroxide. These radical initiators can be used alone or in a combination of two or more. The radical initiators can be used in an amount of 0.1 to 5 parts by weight per 100 parts by weight of the components (A) and (B). A chain-transfer agent can be added. The chain-transfer agent can be 2-mercaptoethanol, butyl mercaptan, n-dodecyl mercaptan, (3-mercaptopropyl)trimethoxysilane, a polydimethylsiloxane possessing a mercaptopropyl group or an analogous compound of mercapto type; methylene chloride, chloroform, carbon tetrachloride, butyl bromide, (3-chloropropyl)trimethoxysilane or an analogous halogenated compound.

In the manufacture of the polymer of vinyl type, after the polymerization, the unreacted residual vinyl monomer can be removed under conditions of heating under vacuum.

To facilitate the preparation of starting material for cosmetic products, the number-average molecular weight of the vinyl polymer which comprises a carbosiloxane dendrimer can be chosen within the range between 3000 and 2 000 000 and preferably between 5000 and 800 000. It can be a liquid, a gum, a paste, a solid, a powder or any other form. The preferred forms are solutions formed by the dilution of a dispersion or of a powder in solvents.

The vinyl polymer can be a dispersion of a polymer of vinyl type having a carbosiloxane dendrimer structure in its molecular side chain, in a liquid such as a silicone oil, an organic oil, an alcohol or water.

The silicone oil can be a dimethylpolysiloxane having the two molecular ends capped with trimethylsiloxy groups, a copolymer of methylphenylsiloxane and of dimethylsiloxane having the two molecular ends capped with trimethylsiloxy groups, a copolymer of methyl(3,3,3-trifluoropropyl)siloxane and of dimethylsiloxane having the two molecular ends capped with trimethylsiloxy groups, or analogous unreactive linear silicone oils, and also hexamethylcyclotrisiloxane, octamethylcyclotetrasiloxane, decamethylcyclopentasiloxane, dodecamethylcyclohexasiloxane or an analogous cyclic compound. In addition to the unreactive silicone oils, modified polysiloxanes possessing functional groups, such as silanol groups, amino groups and polyether groups, on the ends or within the molecular side chains can be used.

The organic oils can be isododecane, liquid paraffin, isoparaffin, hexyl laurate, isopropyl myristate, myristyl myristate, cetyl myristate, 2-octyldodecyl myristate; isopropyl palmitate, 2-ethylhexyl palmitate, butyl stearate, decyl oleate, 2-octyldodecyl oleate, myristyl lactate, cetyl lactate, lanolin acetate, stearyl alcohol, cetearyl alcohol, oleyl alcohol, avocado oil, almond oil, olive oil, cocoa oil, jojoba oil, gum oil, sunflower oil, soybean oil, camelia oil, squalane, castor oil, cottonseed oil, coconut oil, egg yolk oil, polypropylene glycol monooleate, neopentyl glycol 2-ethylhexanoate or an analogous glycol ester oil; triglyceryl isostearate, the triglyceride of a fatty acid of coconut oil, or an analogous oil of a polyhydric alcohol ester; polyoxyethylene lauryl ether, polyoxypropylene cetyl ether or an analogous polyoxyalkylene ether.

The alcohol can be of any type suitable for use together with a starting material for cosmetic products. For example, it can be methanol, ethanol, butanol, isopropanol or analogous lower alcohols.

A solution or a dispersion of the alcohol should have a viscosity within the range from 10 to $10^9$ mPa at 25° C. To improve the sensory use properties in a cosmetic product, the viscosity should be within the range from 100 to $5 \times 10^8$ mPa·s.

The solutions and dispersions can be easily prepared by mixing a vinyl polymer having at least one unit derived from carbosiloxane dendrimer with a silicone oil, an organic oil, an alcohol or water. The liquids can be present in the polymerization stage. In this case, the unreacted residual vinyl monomer should be completely removed by heat treatment of the solution or dispersion under atmospheric pressure or reduced pressure.

In the case of a dispersion, the dispersity of the polymer of vinyl type can be improved by adding a surfactant.

Such a surfactant can be hexylbenzenesulfonic acid, octylbenzenesulfonic acid, decylbenzenesulfonic acid, dodecylbenzenesulfonic acid, cetylbenzenesulfonic acid, myristylbenzenesulfonic acid or anionic surfactants of the sodium salts of these acids; octyltrimethylammonium hydroxide, dodecyltrimethylammonium hydroxide, hexadecyltrimethylammonium hydroxide, octyldimethylbenzylammonium hydroxide, decyldimethylbenzylammonium hydroxide, dioctadecyldimethylammonium hydroxide, (beef tallow)trimethylammonium hydroxide, (coconut oil)trimethylammonium hydroxide, or an analogous cationic surfactant; a polyoxyalkylene alkyl ether, a polyoxyalkylene alkylphenol, a polyoxyalkylene alkyl ester, the sorbitol ester of polyoxyalkylene, polyethylene glycol, polypropylene glycol, an ethylene oxide additive of diethylene glycol trimethylnonanol, and nonionic surfactants of polyester type, and also mixtures.

In the dispersion, a mean particle diameter of the polymer of vinyl type can be within a range of between 0.001 and 100 microns and preferably between 0.01 and 50 microns. The reason for this is that, outside the recommended range, a cosmetic product mixed with the emulsion will not have a nice enough feel on the skin or to the touch, or sufficient spreading properties or a pleasant feel.

A vinyl polymer contained in the dispersion or the solution can have a concentration within a range of between 0.1% and 95% by weight and preferably between 5% and 85% by weight. However, to facilitate the handling and the preparation of the mixture, the range should preferably be between 10% and 75% by weight.

A vinyl polymer suitable for the invention can also be one of the polymers described in the examples of Patent Application EP 0 963 751.

According to a preferred embodiment, a vinyl polymer grafted with a carbosiloxane dendrimer can result from the polymerization:

of 0 to 99.9 parts by weight of one or more acrylate or methacrylate monomer(s); and of 100 to 0.1 parts by weight of an acrylate or methacrylate monomer of a tri[tri(trimethylsiloxy)silylethyldimethylsiloxy]silylpropyl carbosiloxane dendrimer.

The monomers (A1) and (B1) correspond respectively to specific monomers (A) and (B).

According to one embodiment, a vinyl polymer having at least one unit derived from carbosiloxane dendrimer can comprise a unit derived from tri[tri(trimethylsiloxy)silylethyldimethylsiloxy]silylpropyl carbosiloxane dendrimer corresponding to one of the formulae:

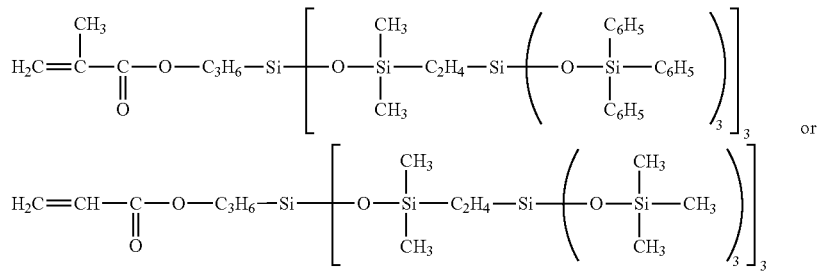

According to a preferred mode, a vinyl polymer having at least one unit derived from carbosiloxane dendrimer used in the invention comprises at least one butyl acrylate monomer.

According to one embodiment, a vinyl polymer can additionally comprise at least one fluorinated organic group.

Structures in which the polymerized vinyl units constitute the backbone and carbosiloxane dendritic structures and also fluorinated organic groups are attached to side chains are particularly preferred.

The fluorinated organic groups can be obtained by replacing with fluorine atoms all or some of the hydrogen atoms of methyl, ethyl, propyl, isopropyl, butyl, isobutyl, tert-butyl, pentyl, neopentyl, hexyl, cyclohexyl, heptyl, octyl, nonyl, decyl, undecyl, dodecyl, tridecyl, tetradecyl, hexadecyl and octadecyl groups and of other alkyl groups of 1 to 20 carbon atoms, and also alkyloxyalkylene groups of 6 to 22 carbon atoms.

The groups represented by the formula $-(CH_2)_x-(CF_2)_y-R^{13}$ are suggested as examples of fluoroalkyl groups obtained by substituting fluorine atoms for hydrogen atoms of alkyl groups. In the formula, the index "x" is 0, 1, 2 or 3, and "y" is an integer from 1 to 20. $R^{13}$ is an atom or a group chosen from a hydrogen atom, a fluorine atom, $-CH(CF_3)_2-$ or $CF(CF_3)_2$. Such fluorine-substituted alkyl groups are exemplified by linear or branched polyfluoroalkyl or perfluoroalkyl groups represented by the formulae presented below: $-CF_3$, $-C_2F_5$, $-nC_3F_7$, $-CF(CF_3)_2$, $-nC_4F_9$, $CF_2CF(CF_3)_2$, $-nC_5F_{11}$, $-nC_6F_{13}$, $-nC_8F_{17}$, $CH_2CF_3$, $-CH(CF_3)_2$, $CH_2CH(CF_3)_2$ $-CH_2(CF_2)_2F$, $-CH_2(CF_2)_3F$, $-CH_2(CF_2)_4F$, $-CH_2(CF_2)_6F$, $-CH_2(CF_2)_8F$, $-CH_2CH_2CF_3$, $-CH_2CH_2(CF_2)_2F$, $-CH_2CH_2(CF_2)_3F$, $-CH_2CH_2(CF_2)_4F$, $-CH_2CH_2(CF_2)_6F$, $-CH_2CH_2(CF_2)_8F$, $-CH_2CH_2(CF_2)_{10}F$, $-CH_2CH_2(CF_2)_{12}F$, $-CH_2CH_2(CF_2)_{14}F$, $-CH_2CH_2(CF_2)_{16}F$, $-CH_2CH_2CH_2CF_3$, $-CH_2CH_2CH_2(CF_2)_2F$, $-CH_2CH_2CH_2(CF_2)_2H$, $-CH_2(CF_2)_4H$ and $-CH_2CH_2(CF_2)_3H$.

The groups represented by $-CH_2CH_2-(CF_2)_m-CFR^{14}-[OCF_2CF(CF_3)]_n-OC_3F_7$ are suggested as fluoroalkyloxyfluoroalkylene groups obtained by substituting fluorine atoms for hydrogen atoms of alkyloxyalkylene groups. In the formula, the index "m" is 0 or 1, "n" is 0, 1, 2, 3, 4 or 5, and $R^{14}$ is a fluorine atom or $CF_3$. Such fluoroalkyloxyfluoroalkylene groups are exemplified by the perfluoroalkyloxyfluoroalkylene groups represented by the formulae presented below: $-CH_2CH_2CF(CF_3)-[OCF_2CF(CF_3)]_n-OC_3F_7$, $-CH_2CH_2CF_2CF_2-[OCF_2CF(CF_3)]_n-OC_3F_7$.

The number-average molecular weight of the vinyl polymer used in the present invention can be between 3000 and 2 000 000 and more preferably between 5000 and 800 000.

This type of fluorinated vinyl polymer can be obtained by addition:
of a vinyl monomer (M2) without a fluorinated organic group,
to a vinyl monomer (M1) comprising fluorinated organic groups, and
a carbosiloxane dendrimer (B) as defined above, of general formula (I) as defined above,
by subjecting them to a copolymerization.

Thus, according to one embodiment, a composition of the invention can comprise a vinyl polymer having at least one unit derived from carbosiloxane dendrimer and resulting from the copolymerization of a vinyl monomer (M1) as defined above, optionally of a vinyl monomer (M2) as defined above, and of a carbosiloxane dendrimer (B) as defined above,
the said vinyl polymer having a copolymerization ratio of the monomer (M1) to the monomer (M2) of 0.1 to 100:99.9 to 0% by weight, and a copolymerization ratio of the sum of the monomers (M1) and (M2) to the monomer (B) of 0.1 to 99.9:99.9 to 0.1% by weight.

The vinyl monomers (M1) comprising fluorinated organic groups in the molecule are preferably monomers represented by the general formula:

$(CH_2)=CR^{15}COOR^f$.

In this formula, $R^{15}$ is a hydrogen atom or a methyl group and $R^f$ is a fluorinated organic group exemplified by the fluoroalkyl and fluoroalkyloxyfluoroalkylene groups described above. The compounds represented by the formulae presented below are suggested as specific examples of the component (M1). In the formulae present below, "z" is an integer from 1 to 4.

$CH_2=CCH_3COO-CF_3$, $CH_2=CCH_3COO-C_2F_5$, $CH_2=CCH_3COO$-$nC_3F_7$, $CH_2=CCH_3COO-CF(CF_3)_2$, $CH_2=CCH_3COO$-$nC_4F_9$, $CH_2=CCH_3COO-CF(CF_3)_2$, $CH_2=CCH_3COO$-$nC_5F_{11}$, $CH_2=CCH_3COO$-$nC_6F_{13}$, $CH_2=CCH_3COO$-$nC_8F_{17}$, $CH_2=CCH_3COO-CH_2CF_3$, $CH_2=CCH_3COO-CH(CF_3)_2$, $CH_2=CCH_3COO-CH_2CH(CF_3)_2$, $CH_2=CCH_3COO-CH_2(CF_2)_2F$, $CH_2=CCH_3COO-CH_2(CF_2)_2F$, $CH_2=CCH_3COO-CH_2(CF_2)_4F$, $CH_2=CCH_3COO-CH_2(CF_2)_6F$, $CH_2=CCH_3COO-CH_2(CF_2)_8F$, $CH_2=CCH_3COO-CH_2CH_2CF_3$, $CH_2=CCH_3COO-CH_2CH_2(CF_2)_2F$, $CH_2=CCH_3COO-CH_2CH_2(CF_2)_3F$, $CH_2=CCH_3COO-$ $CH_2CH_2(CF_2)_4F$, $CH_2=CCH_3COO-CH_2CH_2(CF_2)_6F$, $CH_2=CCH_3COO-CH_2CH_2(CF_2)_8F$, $CH_2=CCH_3COO-CH_2CH_2(CF_2)_{10}F$, $CH_2=CCH_3COO-CH_2CH_2(CF_2)_{12}F$, $CH_2=CCH_3COO-CH_2CH_2(CF_2)_{14}F$, $CH_2=CCH_3COO-CH_2-CH_2-(CF_2)_{16}F$, $CH_2=CCH_3COO-CH_2CH_2CH_2CF_3$, $CH_2=CCH_3COO-CH_2CH_2CH_2(CF_2)_2F$, $CH_2=CCH_3COO-CH_2CH_2CH_2(CF_2)_2H$, $CH_2=CCH_3COO-CH_2(CF_2)_4H$, $CH_2=CCH_3COO-(CF_2)_3H$, $CH_2=CCH_3COO-CH_2CH_2CF(CF_3)-[OCF_2-CF(CF_3)]_z-OC_3F_7$, $CH_2=CCH_3COO-CH_2CH_2CF_2CF_2-[OCF_2-CF(CF_3)]_z-OC_3F_7$, $CH_2=CHCOO-CF_3$, $CH_2=CHCOO-C_2F_5$, $CH_2=CHCOO-nC_3F_7$, $CH_2=CHCOO-CF(CF_3)_2$, $CH_2=CHCOO-nC_4F_9$, $CH_2=CHCOO-CF_2CF(CF_3)_2$, $CH_2=CHCOO-nC_5F_{11}$, $CH_2=CHCOO-nC_6F_{13}$, $CH_2=CHCOO-nC_8F_{17}$, $CH_2=CHCOO-CH_2CF_3$, $CH_2=CHCOO-CH(CF_3)_2$, $CH_2=CHCOO-CH_2CH(CF_3)_2$, $CH_2=CHCOO-CH_2(CF_2)_2F$, $CH_2=CHCOO-CH_2(CF_2)_3F$, $CH_2=CHCOO-CH_2(CF_2)_4F$, $CH_2=CHCOO-CH_2(CF_2)_6F$, $CH_2=CHCOO-CH_2(CF_2)_8F$, $CH_2=CHCOO-CH_2CH_2CF_3$, $CH_2=CHCOO-CH_2CH_2(CF_2)_2F$, $CH_2=CHCOO-CH_2CH_2(CF_2)_3F$, $CH_2=CHCOO-CH_2CH_2(CF_2)_4F$, $CH_2=CHCOO-CH_2CH_2(CF_2)_6F$, $CH_2=CHCOO-CH_2CH_2(CF_2)_8F$, $CH_2=CHCOO-CH_2CH_2(CF_2)_{10}F$, $CH_2=CHCOO-CH_2CH_2-(CF_2)_{12}F$, $CH_2=CHCOO-CH_2CH_2(CF_2)_{14}F$, $CH_2=CHCOO-CH_2CH_2(CF_2)_{16}F$, $CH_2=CHCOO-CH_2CH_2CH_2CF_3$, $CH_2=CHCOO-CH_2CH_2CH_2(CF_2)_2F$, $CH_2=CHCOO-CH_2CH_2CH_2(CF)_2H$, $CH_2=CHCOO-CH_2(CF_2)_4H$, $CH_2=CHCOO-CH_2CH_2(CF_2)_3H$, $CH_2=CHCOO-CH_2CH_2CF(CF_3)-[OCF_2-CF(CF_3)]_z-OC_3F_7$, $CH_2=CHCOO-CH_2CH_2CF_2CF_2(CF_3)-[OCF_2-CF(CF_3)]_2-OC_3F_7$.

Among these, the vinyl polymers represented by the formulae presented below are preferred:
$CH_2=CHCOO-CH_2CH_2(CF_2)_6F$, $CH_2=CHCOO-CH_2CH_2(CF_2)_8F$, $CH_2=CCH_3COO-CH_2CH_2(CF_2)_6F$, $CH_2=CCH_3COO-CH_2CH_2(CF_2)_8F$, $CH_2=CHCOO-CH_2CF_3$, $CH_2=CCH_3COO-CH_2CF_3$.

The vinyl polymers represented by the formulae presented below are particularly preferred:
$CH_2=CHCOO-CH_2CF_3$, $CH_2=CCH_3COO-CH_2CF_3$.

The vinyl monomers (M2) which do not comprise fluorinated organic groups in the molecule can be any monomers having radically polymerizable vinyl groups which are exemplified, for example, by methyl acrylate, methyl methacrylate, ethyl acrylate, ethyl methacrylate, n-propyl acrylate, n-propyl methacrylate, isopropyl acrylate, isopropyl methacrylate and other lower alkyl acrylates or methacrylates; glycidyl acrylate, glycidyl methacrylate, n-butyl acrylate, n-butyl methacrylate, isobutyl acrylate, isobutyl methacrylate, tert-butyl acrylate, tert-butyl methacrylate, n-hexyl acrylate, n-hexyl methacrylate, cyclohexyl acrylate, cyclohexyl methacrylate, 2-ethylhexyl acrylate, 2-ethylhexyl methacrylate, octyl acrylate, octyl methacrylate, lauryl acrylate, lauryl methacrylate, stearyl acrylate, stearyl methacrylate and other higher acrylates and methacrylates; vinyl acetate, vinyl propionate and other lower fatty acid vinyl esters; vinyl butyrate, vinyl caproate, vinyl 2-ethylhexanoate, vinyl laurate, vinyl stearate and other higher fatty acid esters; styrene, vinyltoluene, benzyl acrylate, benzyl methacrylate, phenoxyethyl acrylate, phenoxyethyl methacrylate, vinylpyrrolidone and other vinylaromatic monomers; dimethylaminoethyl acrylate, dimethylaminoethyl methacrylate, diethylaminoethyl acrylate, diethylaminoethyl methacrylate and other aminovinyl monomers, acrylamide, methacrylamide, N-methylolacrylamide, N-methylolmethacrylamide, N-methoxymethylacrylamide, N-methoxymethylmethacrylamide, isobutoxymethoxyacrylamide, isobutoxymethoxymethacrylamide, N, N-di methylacrylamide, N,N-dimethylmethacrylamide and other vinylamide monomers; hydroxyethyl acrylate, hydroxyethyl methacrylate, acrylic acid hydroxypropyl alcohol, methacrylic acid hydroxypropyl alcohol and other hydroxyvinyl monomers; acrylic acid, methacrylic acid, itaconic acid, crotonic acid, fumaric acid, maleic acid and other vinylcarboxylic acid monomers; tetrahydrofurfuryl acrylate, tetrahydrofurfuryl methacrylate, butoxyethyl acrylate, butoxyethyl methacrylate, ethoxydiethylene glycol acrylate, ethoxydiethylene glycol methacrylate, polyethylene glycol acrylate, polyethylene glycol methacrylate, polypropylene glycol monoacrylate, polypropylene glycol monomethacrylate, hydroxybutyl vinyl ether, cetyl vinyl ether, 2-ethylhexyl vinyl ether and other vinyl monomers having an ether bond; acryloyloxypropyltrimethoxysilane, methacryloyloxypropyltrimethoxysilane, polydimethylsiloxanes comprising acryloyl or methacryloyl groups at one of the ends, polydimethylsiloxanes comprising alkenylaryl groups at one of the ends and other silicone compounds having unsaturated groups; butadiene; vinyl chloride; vinylidene chloride, acrylonitrile, methacrylonitrile; dibutyl fumarate; maleic anhydride; dodecylsuccinic anhydride; acryl glycidyl ether, methacryl glycidyl ether, 3,4-epoxycyclohexylmethyl acrylate, 3,4-epoxycyclohexylmethyl methacrylate, alkali metal salts, ammonium salts and organic amine salts of acrylic acid, of methacrylic acid, of itaconic acid, of crotonic acid, of fumaric acid, of maleic acid and of other radically polymerizable unsaturated carboxylic acids, radically polymerizable unsaturated monomers comprising sulfonic acid groups, such as styrenesulfonic acid, and also their alkali metal salts, their ammonium salts and their organic amine salts; the quaternary ammonium salts resulting from acrylic acid or methacrylic acid, such as 2-hydroxy-3-methacryloyloxypropyltrimethylammonium chloride, methacrylic acid esters of a tertiary amine alcohol, such as the diethylamine ester of methacrylic acid, and their quaternary ammonium salts.

In addition, it is also possible to use, as vinyl monomers (M2), the polyfunctional vinyl monomers which are exemplified, for example, by trimethylolpropane triacrylate, trimethylolpropane trimethacrylate, pentaerythrityl triacrylate, pentaerythrityl trimethacrylate, ethylene glycol diacrylate, ethylene glycol dimethacrylate, tetraethylene glycol diacrylate, tetraethylene glycol dimethacrylate, polyethylene glycol diacrylate, polyethylene glycol dimethacrylate, 1,4-butanediol diacrylate, 1,4-butanediol dimethacrylate, 1,6-hexanediol diacrylate, 1,6-hexanediol dimethacrylate, neopentyl glycol diacrylate, neopentyl glycol dimethacrylate, trimethylolpropane ethoxylate triacrylate, trimethylolpropane ethoxylate trimethacrylate, tris(2-hydroxyethyl)isocyanurate diacrylate, tris(2-hydroxyethyl)isocyanurate dimethacrylate, tris(2-hydroxyethyl)isocyanurate triacrylate, tris(2-hydroxyethyl)isocyanurate trimethacrylate, polydimethylsiloxane, the two ends of the molecular chain of which are blocked with alkenylaryl groups, and other silicone compounds having unsaturated groups.

As regards the abovementioned ratio in which (M1) and (M2) are copolymerized, the ratio by weight of (M1) to (M2) is preferably within the range from 1:99 to 100:0.

Y can be chosen, for example, from organic groups having acrylic or methacrylic groups, organic groups having an alkenylaryl group, or alkenyl groups with from 2 to 10 carbon atoms.

The organic groups having acrylic or methacrylic groups and the alkenylaryl groups are as defined above.

Mention may be made, among the compounds (B), for example, of the following compound:

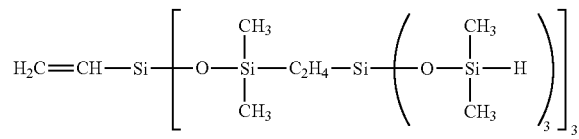

The carbosiloxane dendrimers (B) can be prepared using the process for preparing branched siloxane/silalkylene copolymers described in the document EP 1 055 674.

For example, they can be prepared by subjecting organic alkenyl silicone compounds and silicone compounds comprising hydrogen atoms bonded to the silicon, represented by the formula (IV) as defined above, to a hydrosilylation reaction.

The copolymerization ratio (by weight) of the monomer (B) to the monomers (M1) and (M2) is preferably within the range from 1:99 to 99:1 and even more preferably within the range from 5:95 to 95:5.

Amino groups can be introduced into the side chains of the vinyl polymer using, included in the component (M2), vinyl monomers comprising amino groups, such as dimethylaminoethyl acrylate, dimethylaminoethyl methacrylate, diethylaminoethyl acrylate and diethylaminoethyl methacrylate, followed by performing a modification with potassium acetate monochloride, ammonium acetate monochloride, the aminomethylpropanol salt of monochloroacetic acid, the triethanolamine salt of monobromoacetic acid, sodium monochloropropionate, and other alkali metal salts of halogenated fatty acids; otherwise, carboxylic acid groups can be introduced into the side chains of the vinyl polymer using, included in the component (M2), vinyl monomers comprising carboxylic acids, such as acrylic acid, methacrylic acid, itaconic acid, crotonic acid, fumaric acid and maleic acid, and the like, followed by neutralizing the product with triethylamine, diethylamine, triethanolamine and other amines.

A fluorinated vinyl polymer can be one of the polymers described in the examples of Application WO 03/045337.

According to a preferred embodiment, a grafted vinyl polymer within the meaning of the present invention can be conveyed in an oil or a mixture of oils, which are preferably volatile in particular, chosen from silicone oils and hydrocarbon oils and their mixtures.

According to a specific embodiment, a silicone oil suitable for the invention can be cyclopentasiloxane.

According to another specific embodiment, a hydrocarbon oil suitable for the invention can be isododecane.

Vinyl polymers grafted with at least one unit derived from carbosiloxane dendrimer which can be particularly suitable for the present invention are the polymers sold under the names TIB 4-100, TIB 4-101, TIB 4-120, TIB 4-130, TIB 4-200, FA 4002 ID (TIB 4-202), TIB 4-220 and FA 4001 CM (TIB 4-230) by Dow Corning.

According to a specific form of the invention, the lipophilic film-forming polymer(s) are chosen from:

a silicone resin of MQ type of trimethylsiloxysilicate type;
a resin of MQ type of phenylalkylsiloxysilicate type;
a polypropylsilsesquioxane or t-propyl silsesquioxane resin (INCI name: Polypropylsilsesquioxane (and) Isododecane);
a vinyl polymer grafted with at least one unit derived from carbosiloxane dendrimer (INCI name: Acrylates/Polytrimethylsiloxymethacrylate).

According to a specific form of the invention, the lipophilic film-forming polymer is a polypropylsilsesquioxane or t-propyl silsesquioxane resin (INCI name: Polypropylsilsesquioxane (and) Isododecane).

According to one embodiment, the composition according to the present invention comprises the lipophilic film-forming polymer in an active material content of from 0.1% to 20%, in particular from 0.5% to 15%, more particularly from 0.5% to 10% and preferably from 0.5% to 4% by weight, with respect to the total weight of the said composition.

According to a particularly preferred form, the composition in accordance with the invention comprises at least:
a) at least 15.0% by weight, with respect to the total weight of the composition, of at least one non-volatile hydrocarbon oil with a refractive index of greater than or equal to 1.450 chosen from branched $C_{18}$-$C_{36}$ fatty acid triglycerides, diisostearyl malate, tridecyl trimellitate and their mixtures and optionally of at least one non-volatile oil with a refractive index of less than 1.450 chosen in particular from synthetic ethers having from 10 to 40 carbon atoms, in particular dicaprylyl ether, and
b) at least one volatile hydrocarbon oil chosen from $C_8$-$C_{16}$ isoalkanes, in particular isododecane, and
c) at least 8% by weight of ethanol, with respect to the total weight of the composition, and
d) at least one lipophilic film-forming polymer chosen from a silicone resin of MQ type of trimethsiloxysilicate type, a polypropylsilsesquioxane or t-propyl silsesquioxane resin, or a vinyl polymer grafted with at least one unit derived from carbosiloxane dendrimer, and
e) at least one pigment.

Particulate Material

The particulate materials which can be used in the compositions according to the invention can be chosen from pigments, fillers and their mixtures.

The term "pigments" should be understood as meaning white or coloured and inorganic or organic particles which are insoluble in an aqueous solution and which are intended to colour and/or opacify the resulting film.

The term "filler" should be understood as meaning colourless or white solid particles of any shape which are provided in an insoluble form dispersed in the medium of the composition. Of inorganic or organic nature, they make it possible to confer body or firmness on the composition and/or softness and uniformity on the make-up.

Pigments

The pigments can be present in a proportion of from 0.1% to 40% by weight, in particular from 1% to 30% by weight and especially from 5% to 15% by weight, with respect to the total weight of the cosmetic composition.

Mention may be made, as inorganic pigments which can be used in the invention, of titanium, zirconium or cerium oxides, and also zinc, iron or chromium oxides, ferric blue, manganese violet, ultramarine blue and chromium hydrate. Preferably, the composition of the invention comprises at least titanium oxides and iron oxides.

Mention may in particular be made, as inorganic pigments which can be used in the invention, of pearlescent agents.

The term "pearlescent agents" should be understood as meaning coloured particles of any shape, which are or are not iridescent, in particular produced by certain molluscs in their shells or else synthesized, and which exhibit a colour effect via optical interference.

The pearlescent agents can be chosen from pearlescent pigments, such as titanium oxide-coated mica covered with an iron oxide, titanium oxide-coated mica covered with bismuth oxychloride, titanium oxide-coated mica covered with chromium oxide, titanium oxide-coated mica covered with an organic dye and also pearlescent pigments based on bismuth oxychloride. They can also be mica particles, at the surface of which are superposed at least two successive layers of metal oxides and/or of organic colourants.

Examples of nacres that may also be mentioned include natural mica covered with titanium oxide, with iron oxide, with natural pigment or with bismuth oxychloride.

Mention may be made, among the commercially available pearlescent agents, of the Timica, Flamenco and Duochrome pearlescent agents (on a mica base) sold by Engelhard, the Timiron pearlescent agents sold by Merck, the Prestige pearlescent agents on a mica base sold by Eckart and the Sunshine pearlescent agents on a synthetic mica base sold by Sun Chemical.

The pearlescent agents can more particularly have a yellow, pink, red, bronze, orange, brown, gold and/or coppery colour or tint.

Mention may in particular be made, by way of illustration of pearlescent agents which can be used in the context of the present invention, of pearlescent agents of gold colour sold in particular by Engelhard under the names Brilliant Gold 212G (Timica), Gold 222C (Cloisonne), Sparkle Gold (Timica), Gold 4504 (Chromalite) and Monarch Gold 233X (Cloisonne); bronze pearlescent agents sold in particular by Merck under the names Bronze Fine (17384) (Colorona) and Bronze (17353) (Colorona) and by Engelhard under the name Super Bronze (Cloisonne); orange pearlescent agents sold in particular by Engelhard under the names Orange 363C (Cloisonne) and Orange MCR 101 (Cosmica) and by Merck under the names Passion Orange (Colorona) and Matte Orange (17449) (Microna); brown-coloured pearlescent agents sold in particular by Engelhard under the names Nu-Antique Copper 340XB (Cloisonne) and Brown CL4509 (Chromalite); pearlescent agents with a copper glint sold in particular by Engelhard under the name Copper 340A (Timica); pearlescent agents with a red glint sold in particular by Merck under the name Sienna Fine (17386) (Colorona); pearlescent agents with a yellow glint sold in particular by Engelhard under the name Yellow (4502) (Chromalite); red-coloured pearlescent agents with a gold glint sold in particular by Engelhard under the name Sunstone G012 (Gemtone); pink pearlescent agents sold in particular by Engelhard under the name Tan Opale G005 (Gemtone); black pearlescent agents with a gold glint sold in particular by Engelhard under the name Nu-Antique Bronze 240 AB (Timica); blue pearlescent agents sold in particular by Merck under the name Matte Blue (17433) (Microna); white pearlescent agents with a silvery glint sold in particular by Merck under the name Xirona Silver; and golden green pinkish orangey pearlescent agents sold in particular by Merck under the name Indian Summer (Xirona), and their mixtures.

Mention may be made, among the pigments which can be used according to the invention, of those having an optical effect different from a simple conventional colouring effect, that is to say a unified and stabilized effect such as produced by conventional colourants, such as, for example, monochromatic pigments. Within the meaning of the invention, the term "stabilized" means devoid of an effect of variability in the colour with the angle of observation or alternatively in response to a change in temperature.

For example, this material can be chosen from particles with a metallic glint, goniochromatic colouring agents, diffracting pigments, thermochromic agents, optical brighteners and also fibres, in particular interference fibres. Of course, these various materials can be combined so as to provide the simultaneous display of two effects, indeed even of a novel effect in accordance with the invention.

The particles with a metallic glint which can be used in the invention are chosen in particular from:
  particles of at least one metal and/or of at least one metal derivative,
  particles comprising an organic or inorganic substrate, made of one or more material(s), at least partially covered with at least one layer with a metallic glint comprising at least one metal and/or at least one metal derivative, and
  mixtures of the said particles.

Mention may be made, among the metals which can be present in the said particles, for example, of Ag, Au, Cu, Al, Ni, Sn, Mg, Cr, Mo, Ti, Zr, Pt, Va, Rb, W, Zn, Ge, Te, Se and their mixtures or alloys. Ag, Au, Cu, Al, Zn, Ni, Mo, Cr and their mixtures or alloys (for example, bronzes and brasses) are preferred metals.

The term "metal derivatives" denotes compounds derived from metals, in particular oxides, fluorides, chlorides and sulfides.

Mention may be made, by way of illustration of these particles, of aluminium particles, such as those sold under the names Starbrite 1200 EAC® by Silberline and Metalure® by Eckart.

Mention may also be made of metal powders formed of copper or alloy mixtures, such as the references 2844 sold by Radium Bronze, metal pigments, such as aluminium or bronze, for example those sold under the names Rotosafe 700 from Eckart, silica-coated aluminium particles sold under the name Visionaire Bright Silver from Eckart and particles formed of metal alloy, such as powders formed of bronze (copper and zinc alloy) coated with silica sold under the name Visionaire Bright Natural Gold from Eckart.

The particles can also comprise a glass substrate, such as those sold by Nippon Sheet Glass under the names Microglass Metashine.

The goniochromatic colouring agent can be chosen, for example, from interference multilayer structures and liquid crystal colouring agents.

Examples of symmetrical interference multilayer structures which can be used in compositions produced in accordance with the invention are, for example, the following structures: $Al/SiO_2/Al/SiO_2/Al$, pigments having this structure being sold by DuPont de Nemours; $Cr/MgF_2/Al/MgF_2/Cr$, pigments having this structure being sold under the name Chromaflair by Flex; $MoS_2/SiO_2/Al/SiO_2/MoS_2$; $Fe_2O_3/SiO_2/Al/SiO_2/Fe_2O_3$ and $Fe_2O_3/SiO_2/Fe_2O_3/SiO_2/Fe_2O_3$, pigments having these structures being sold under the name Sicopearl by BASF; $MoS_2/SiO_2/mica$-oxide$/SiO_2/MoS_2$; $Fe_2O_3/SiO_2/mica$-oxide$/SiO_2/Fe_2O_3$; $TiO_2/SiO_2/TiO_2$ and $TiO_2/Al_2O_3/TiO_2$; $SnO/TiO_2/SiO_2/TiO_2/SnO$; $Fe_2O_3/SiO_2/Fe_2O_3$; $SnO/mica/TiO_2/SiO_2/TiO_2/mica/SnO$, pigments having these structures being sold under the name Xirona by Merck (Darmstadt). By way of example, these pigments can be pigments with a silica/titanium oxide/tin oxide structure sold under the name Xirona Magic by Merck, pigments with a silica/brown iron oxide structure sold under the name Xirona Indian Summer by Merck and pigments with a silica/titanium oxide/mica/tin oxide structure sold under the name Xirona Caribbean Blue by Merck. Mention may also be made of the Infinite Colors pigments from Shiseido. Different effects are obtained according to the thickness and the nature of the various layers. Thus, with the structure $Fe_2O_3/SiO_2/Al/SiO_2/Fe_2O_3$, the colour changes from green-golden to red-grey for $SiO_2$ layers of 320 to 350 nm; from red to golden for $SiO_2$ layers of 380 to 400 nm; from purple to green for $SiO_2$ layers of 410 to 420 nm; and from copper to red for $SiO_2$ layers of 430 to 440 nm.

Mention may be made, as examples of pigments with a polymeric multilayer structure, of those sold by 3M under the name Color Glitter.

Use may be made, as liquid crystal goniochromatic particles, for example, of those sold by Chenix and of that sold under the name Helicone® HC by Wacker.

Fillers

The fillers which can be used in the composition of the invention can be of organic or inorganic nature and make it possible in particular to confer on it additional properties of improved stability, wear property, coverage and/or mattness.

The content of filler(s) can range from 2% to 20% by weight, in particular from 4% to 12% by weight, with respect to the total weight of the said composition.

The fillers used in the compositions according to the present invention can be of lamellar, globular, spherical or fibrous form or of any other form intermediate between these defined forms.

The fillers according to the invention may or may not be surface-coated, and in particular they may be surface-treated with silicones, amino acids, fluorinated derivatives or any other substance which promotes the dispersion and the compatibility of the filler in the composition.

Mention may be made, as examples of inorganic fillers, of clays, talc, mica, silica, hollow silica microspheres, kaolin, calcium carbonate, magnesium carbonate, hydroxyapatite, boron nitride, glass or ceramic microcapsules, composites of silica and of titanium dioxide, such as the TSG series sold by Nippon Sheet Glass, or hydrophobic silica aerogel particles surface-modified by trimethylsilyl groups.

According to a specific form of the invention, the composition of the invention comprises, as filler, at least hydrophobic silica aerogel particles surface-modified by trimethylsilyl groups and/or a lipophilic clay.

Mention may be made, as hydrophobic silica aerogels which can be used in the invention, for example, of the aerogel sold under the name VM-2260® (INCI name: Silica Silylate) by Dow Corning, the particles of which exhibit a mean size of approximately 1000 microns and a specific surface per unit of weight ranging from 600 to 800 $m^2/g$.

Mention may also be made of the aerogels sold by Cabot under the references Aerogel TLD 201, Aerogel OGD 201, Aerogel TLD 203, Enova® Aerogel MT 1100 and Enova Aerogel MT 1200.

Use will preferably be made of the aerogel sold under the name VM-2270 (INCI name: Silica Silylate) by Dow Corning, the particles of which exhibit a mean size ranging from 5 to 15 microns and a specific surface per unit of weight ranging from 600 to 800 $m^2/g$.

The clays can be natural or synthetic and they are rendered lipophilic by treatment with an alkylammonium salt, such as a $C_{10}$ to $C_{22}$ ammonium chloride, for example distearyldimethylammonium chloride.

They can be chosen from bentonites, in particular hectorites and montmorillonites, beidellites, saponites, nontronites, sepiolites, biotites, attapulgites, vermiculites and zeolites.

They are preferably chosen from hectorites.

Use will in particular be made of a hectorite modified by distearyldimethylammonium chloride, such as the commercial product sold under the name Bentone Gel ISD V® by Elementis.

Mention may be made, as examples of organic fillers, of powders formed of polyamide (Orgasol Nylon® from Atochem), of polyethylene, of poly(methyl methacrylate), of polytetrafluoroethylene (Teflon) or of acrylic acid copolymers (Polytrap from Dow Corning), lauroyl lysine, hollow polymeric microspheres, such as those of polyvinylidene chloride/acrylonitrile, such as Expancel (Nobel Industrie), hexamethylene diisocyanate/trimethylol hexyllactone copolymer powder (Plastic Powder from Toshiki), silicone resin microbeads other than those defined above (Tospearl from Toshiba, for example), synthetic or natural micronized waxes, metal soaps derived from organic carboxylic acids having from 8 to 22 carbon atoms, preferably from 12 to 18 carbon atoms, for example zinc stearate, magnesium stearate, lithium stearate, zinc laurate or magnesium myristate, Polypore® L 200 (Chemdal Corporation) or polyurethane powders, in particular powders formed of crosslinked polyurethane comprising a copolymer, the said copolymer comprising trimethylol hexyllactone. It can in particular be a hexamethylene diisocyanate/trimethylol hexyllactone polymer. Such particles are in particular commercially available, for example under the name Plastic Powder D-400® or Plastic Powder D-800® from Toshiki, and their mixtures.

Additives

The compositions according to the invention can also comprise additional cosmetic ingredients conventionally employed in the formulation of specific formulation forms generally adjusted from the viewpoint of the keratinous substance targeted. This or these additional cosmetic ingredients can in particular be chosen from waxes, pasty fatty substances, surfactants, lipophilic gelling agents, dispersing agents, active agents, preservatives, antioxidants, solvents, fragrances, sunscreens, bactericides, odour absorbers, fat-soluble dyes and their mixtures.

The amounts of the additional cosmetic ingredients are those conventionally used in the field under consideration, for example from 0.01% to 20% of the total weight of the composition and preferably from 0.01% to 10% of the total weight of the composition.

Of course, a person skilled in the art will take care to choose the optional additional ingredients and/or their amounts so that the advantageous properties of the composition according to the invention are not, or not substantially, detrimentally affected by the envisaged addition.

The fat-soluble dyes are, for example, Sudan Red, DC Red 17, DC Green 6, β-carotene, soybean oil, Sudan Brown, DC Yellow 11, DC Violet 2, DC Orange 5 and quinoline yellow.

Silicone Surfactant

According to a specific form, the compositions in accordance with the invention can additionally comprise a silicone surfactant chosen in particular from oxyalkylenated and preferably oxyethylenated polydimethylsiloxanes.

Preferably, the silicone surfactant comprises polyoxyethylene chains on the main chain (side or pendent polyoxyethylene chains).

The number of alkylene oxide units can range from 2 to 50 and preferably from 5 to 20.

Such silicone surfactants are in particular those called PEG-10 dimethicone, sold by Shin-Etsu under the name KF-6017.

The silicone surfactant can be present in the composition according to the invention in an amount ranging from 0.01% to 5% by weight and preferably from 0.1% to 3% by weight, with respect to the total weight of the composition.

Dispersing Agent

Advantageously, a composition according to the invention can additionally comprise a dispersing agent.

Such a dispersing agent can be a surfactant, an oligomer, a polymer or a mixture of several of them.

According to a specific embodiment, a dispersing agent in accordance with the invention is a surfactant.

Active Agent

For a care application in particular, a composition according to the invention can comprise at least one moisturizing agent (also known as humectant).

Preferably, the moisturizing agent is glycerol.

The moisturizing agent or agents can be present in the composition in a content ranging from 0.1% to 15% by weight, in particular from 0.5% to 10% by weight, indeed even from 1% to 6% by weight, with respect to the total weight of the said composition.

Mention may be made, as other active agents which can be used in the composition of the invention, for example, of vitamins, sunscreens and their mixtures.

Preferably, a composition according to the invention comprises at least one active agent.

It is a matter of routine operations for a person skilled in the art to adjust the natures and the amounts of the additives present in the compositions in accordance with the invention so that the cosmetic properties desired for the latter are not affected thereby.

Formulation Forms

The compositions according to the invention can be provided in the form of a foundation, concealer, mascara or lipstick.

A cosmetic composition of the invention is provided in the form of an anhydrous liquid product. In particular, a cosmetic composition of the invention can be provided in the form of a liquid foundation, a product for making up the body, a concealer or a make-up base.

According to one embodiment, a composition of the invention can advantageously be provided in the form of a composition for caring for the skin of the body or of the face, in particular of the face.

According to another embodiment, a composition of the invention can advantageously be provided in the form of a make-up base composition.

According to another embodiment, a composition of the invention can advantageously be provided in the form of a foundation.

Such compositions are prepared in particular according to the general knowledge of a person skilled in the art.

The expressions "between . . . and . . . " and "ranging from . . . to . . . " should be understood as being inclusive of the limits, unless otherwise specified.

The invention is illustrated in more detail by the examples and figures presented below. Unless otherwise indicated, the amounts shown are expressed as percentages by weight.

EXAMPLES

The two following anhydrous liquid formulations were prepared:

| Phase | Ingredients | Example 1 (invention) | Example 2 (outside the invention) |
|---|---|---|---|
| A | Diisostearyl Malate | 20 | 20 |
| | Tridecyl Trimellitate | 15 | 15 |
| | C18-36 Acid Triglyceride | 10 | 10 |
| | Isododecane | q.s. for 100 | q.s. for 100 |
| | Ethylhexyl Methoxycinnamate (Parsol MCX ® - DSM) | 5 | 5 |
| | Polypropylsilsesquioxane (and) Isododecane (72% of active material), sold under the reference Dow Corning 680 ID Fluid by Dow Corning | 1 (0.72 A.M.*) | — |
| B | Disteardimonium Hectorite/Propylene Carbonate/Isododecane (10/3/87), sold under the reference Bentone Gel ISO V by Elementis | 3 | 3 |
| C | Dodecamethylpentasiloxane | 3 | 3 |
| | Dicaprylyl Ether | 9.96 | 9.96 |
| | Silica Silylate (VM-2260 ® - Dow Corning) | 0.2 | 0.2 |
| D | PEG-10 Dimethicone (KF 6017 ® - Shin-Etsu) | 1.5 | 1.5 |
| E | 96° Denatured Ethanol | 12.48 | 12.48 |
| F | Titanium Dioxide coated with Aluminium Stearoyl Glutamate | 10.41 | 10.41 |
| | Red Iron Oxide coated with Aluminium Stearoyl Glutamate | 0.48 | 0.48 |
| | Black Iron Oxide coated with Aluminium Stearoyl Glutamate | 0.19 | 0.19 |
| | Yellow Iron Oxide coated with Aluminium Stearoyl Glutamate | 1.9 | 1.9 |
| | Synthetic Fluorphlogopite | 1.44 | 1.44 |
| | Centrifuging 1 hour: 1000 rpm at ambient temperature (25° C.) | Transparent | Cloudy |
| | "Natural" sedimentation 24 hours in a 30 ml flask at ambient temperature (25° C.) | Transparent | Translucent with suspended particle |

A.M.* = active material

Procedure:

The constituents of the phase A were weighed out in the main beaker and stirring was carried out with a Moritz stirrer while maintaining at ambient temperature. The stirring rate was adjusted as a function of the amount manufactured and of the viscosity of the mixture. Stirring was maintained until a homogeneous mixture was obtained. The phase B was added with stirring. Stirring was maintained until a homogeneous mixture (absence of clumps) was obtained. The phase C was prepared separately by dispersing the Silica Silylate in the mixture of the two oils in a beaker using a spatula. The mixture C was added while stirring with the Moritz stirrer. Stirring was maintained until a homogeneous mixture was obtained. The phases D and E were added with stirring. Stirring was maintained for 10 minutes. The stirring rate was adjusted as a function of the amount manufactured and of the viscosity of the mixture. Finally, the phase F was added while stirring with the Moritz stirrer. Stirring was maintained until a homogeneous mixture and a good pigmentary dispersion (absence of clumps) were obtained. Packaging was subsequently carried out rapidly.

It was observed that Example 1 according to the invention, comprising the lipophilic film-forming polymer of the silsesquioxane resin type, makes it possible, after centrifuging at 1000 rpm for one hour, at ambient temperature and standing for 24 hours, at ambient temperature, in a 30 ml flask, to give a "clean" sedimentation of the pigments which is reflected by a transparent salting out and by a ready and homogeneous redispersion of the cake, in contrast to Example 2 devoid of lipophilic film-forming polymer.

The composition of Example 1 also exhibited a non-greasy and non-tacky oily sensation.

Examples 3 to 7

Examples 3 and 4 of the invention and Examples 5, 6 and 7 (outside the invention) were prepared under the same conditions as Examples 1 and 2.

ambient temperature and standing for 24 hours, at ambient temperature, in a 30 ml flask, to give a "clean" sedimentation of the pigments which is reflected by a transparent salting out and by a ready and homogeneous redispersion of the cake, in contrast to:

Example 5 comprising the film-forming polymer Acrylic Acid/Isobutyl Acrylate/Isobornyl Acrylate Copolymer, Example 6 comprising the film-forming polymer Hydrogenated Polybutadiene/Polydiene, Example 7 comprising the film-forming polymer Acrylates/Dimethicone Copolymer.

Examples 3 and 4 of the invention also exhibited a non-fatty and non-tacky oily sensation.

| Phase | Ingredients | Ex. 3 | Ex. 4 | Ex. 5 | Ex. 6 | Ex. 7 |
|---|---|---|---|---|---|---|
| A | Diisostearyl Malate | 20 | 20 | 20 | 20 | 20 |
|  | Tridecyl Trimellitate | 15 | 15 | 15 | 15 | 15 |
|  | C18-36 Acid Triglyceride | 10 | 10 | 10 | 10 | 10 |
|  | Isododecane | q.s. for 100 | q.s. for 100 | q.s. for 100 | q.s. for 100 | q.s. for 100 |
|  | Ethylhexyl Methoxycinnamate (Parsol MCX ® - DSM) | 5 | 5 | 5 | 5 | 5 |
|  | Trimethylsiloxysilicate (SR1000 ® - General Electric) | 0.72 A.M.* | — | — | — | — |
|  | Acrylates/Polytrimethylsiloxymethacrylate (FA 4002 ID Silicone Acrylate ® - Dow Corning) | — | 1.8 (0.72 A.M.*) | — | — | — |
|  | Acrylic Acid/Isobutyl Acrylate/Isobornyl Acrylate Copolymer (Mexomer PAS ® - Chimex) | — | — | 1.44 (0.72 A.M.*) | — | — |
|  | Hydrogenated Polybutadiene/Polydiene (Mexomer PBI ® - Chimex) | — | — | — | 2.44 (0.72 A.M.*) | — |
|  | Acrylates/Dimethicone Copolymer (KP550 ® - Shin-Etsu) | — | — | — | — | 1.8 (0.72 A.M.*) |
| B | Disteardimonium Hectorite/Propylene Carbonate/Isododecane (Oct. 3, 1987), sold under the reference Bentone Gel ISD V by Elementis | 3 | 3 | 3 | 3 | 3 |
| C | PEG-10 Dimethicone (KF 6017 ® - Shin-Etsu) | 1.5 | 1.5 | 1.5 | 1.5 | 1.5 |
| D | Silica Silylate (VM-2260 ® - Dow Corning) | 0.2 | 0.2 | 0.2 | 0.2 | 0.2 |
|  | Dodecamethylpentasiloxane | 3 | 3 | 3 | 3 | 3 |
|  | Dicaprylyl Ether | 9.96 | 9.96 | 9.96 | 9.96 | 9.96 |
| E | 96° Denatured Ethanol | 12.48 | 12.48 | 12.48 | 12.48 | 12.48 |
| F | Titanium Dioxide coated with Aluminium Stearoyl Glutamate | 10.41 | 10.41 | 10.41 | 10.41 | 10.41 |
|  | Red Iron Oxide coated with Aluminium Stearoyl Glutamate | 0.48 | 0.48 | 0.48 | 0.48 | 0.48 |
|  | Black Iron Oxide coated with Aluminium Stearoyl Glutamate | 0.19 | 0.19 | 0.19 | 0.19 | 0.19 |
|  | Yellow Iron Oxide coated with Aluminium Stearoyl Glutamate | 1.9 | 1.9 | 1.9 | 1.9 | 1.9 |
|  | Mica (Synthetic Fluorphlogopite) | 1.44 | 1.44 | 1.44 | 1.44 | 1.44 |

A.M.* = active material

The results of the appearance of the compositions after centrifuging for 1 hour at 1000 rpm and standing for 24 h in a 30 ml flask are shown in the following table:

| Observation | Ex. 3 | Ex. 4 | Ex. 5 | Ex. 6 | Ex. 7 |
|---|---|---|---|---|---|
| Centrifuging 1 hour: 1000 rpm at ambient temperature (25° C.) | Transparent | Transparent | Cloudy | Cloudy | Cloudy |
| "Natural" sedimentation 24 hours in a 30 ml flask | Transparent | Transparent | Translucent with suspended particle | Translucent with suspended particle | Translucent with suspended particle |

It was observed that Example 3 according to the invention, comprising the lipophilic film-forming polymer of the MQ resin type, and Example 4 according to the invention, comprising the lipophilic film-forming polymer of the vinyl polymer grafted with a carbosiloxane dendrimer type, make it possible, after centrifuging at 1000 rpm for one hour, at

The invention claimed is:

1. An anhydrous liquid composition comprising, in a physiologically acceptable medium:
   a) an oily phase comprising:
      i) from 45% to 55% by weight of non-volatile oil, wherein the non-volatile oil is a mixture of diisostearyl Malate, Tridecyl Trimellitate, C18-36 fatty acid triglyceride and dicaprylyl ether
      ii) from 10-30% by weight of isododecane:
   b) 8-40% by weight of ethanol
   c) from 0.1 to 20% by weight of lipophilic film-forming polymer chosen from
      (i) trimethyl siloxysilicate,
      (ii) polypropylsilsesquioxane,
      (iii) acrylates/polytrimethyl siloxymethacrylate
   d) at least one particulate material, wherein the at least one particulate material comprises titanium oxide and iron oxide and
   e) silicone surfactant, wherein the silicone surfactant is PEG-10 dimethicone wherein the at least one non-volatile oil is present in a concentration ranging from 30% to 60% by weight with respect to the total weight of the composition.

2. The anhydrous liquid composition according to claim 1, further comprising at least one volatile silicone oil.

3. The anhydrous liquid composition according to claim 1, comprising, as filler, at least hydrophobic silica aerogel particles surface-modified by trimethylsilyl groups and/or a lipophilic clay.

4. The anhydrous liquid composition according to claim 1, the composition exhibiting a viscosity ranging from 0.02 to 0.8 Pa·s.

5. A method for coating skin, comprising:
applying to the skin the anhydrous liquid composition according to claim 1.

* * * * *

UNITED STATES PATENT AND TRADEMARK OFFICE
CERTIFICATE OF CORRECTION

| | |
|---|---|
| PATENT NO. | : 11,497,705 B2 |
| APPLICATION NO. | : 15/762879 |
| DATED | : November 15, 2022 |
| INVENTOR(S) | : Euriel Clavel |

It is certified that error appears in the above-identified patent and that said Letters Patent is hereby corrected as shown below:

In the Claims

In Column 36, Claim 1, Line 54, delete "C18-36" and insert -- $C_{18}$-$C_{36}$ --, therefor.

Signed and Sealed this
Twenty-sixth Day of December, 2023

Katherine Kelly Vidal
*Director of the United States Patent and Trademark Office*